(12) United States Patent
Ito et al.

(10) Patent No.: US 9,610,367 B2
(45) Date of Patent: Apr. 4, 2017

(54) PARTICLE AND CONTRAST AGENT HAVING THE PARTICLE

(75) Inventors: Shinzaburo Ito, Kyoto (JP); Masato Minami, Kawasaki (JP); Tatsuki Fukui, Yokohama (JP); Kouichi Kato, Yokohama (JP); Fumio Yamauchi, Kyoto (JP); Yoshinori Tomida, Atsugi (JP); Satoshi Yuasa, Yokohama (JP); Tetsuya Yano, Kyoto (JP); Satoshi Ogawa, Kyoto (JP); Kengo Kanazaki, Kyoto (JP); Atsushi Takahashi, Kawasaki (JP); Daisuke Sasaguri, Yokohama (JP); Hiroyuki Aoki, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 1025 days.

(21) Appl. No.: 13/817,711

(22) PCT Filed: Aug. 23, 2011

(86) PCT No.: PCT/JP2011/069370
§ 371 (c)(1),
(2), (4) Date: Apr. 25, 2013

(87) PCT Pub. No.: WO2012/026608
PCT Pub. Date: Mar. 1, 2012

(65) Prior Publication Data
US 2013/0209367 A1    Aug. 15, 2013

(30) Foreign Application Priority Data

Aug. 24, 2010 (JP) .................................. 2010-187667
Apr. 8, 2011 (JP) .................................. 2011-086280

(51) Int. Cl.
*A61K 9/00* (2006.01)
*A61K 49/00* (2006.01)
(Continued)

(52) U.S. Cl.
CPC ........ *A61K 49/0093* (2013.01); *A61K 9/5153* (2013.01); *A61K 49/0034* (2013.01);
(Continued)

(58) Field of Classification Search
CPC .................................................. A61K 49/0093
See application file for complete search history.

(56) References Cited

U.S. PATENT DOCUMENTS

2009/0004118 A1* 1/2009 Nie .................. A61K 47/48076
424/9.35
2011/0081294 A1    4/2011 Fukui et al.
(Continued)

FOREIGN PATENT DOCUMENTS

WO    WO 2007028118 A2 *  3/2007 ........... C07D 401/06
WO    2008/054874 A2    5/2008
(Continued)

OTHER PUBLICATIONS

Vishal Saxena et al., "Enhanced Photo-Stability, Thermal-Stability and Aqueous-Stability of Indocyanine Green in Polymeric Nanoparticulate Systems," 74 J. Photochem. Photobiol. B: Biology 29-38 (2004) (XP002664214).
(Continued)

*Primary Examiner* — Paul Dickinson
(74) *Attorney, Agent, or Firm* — Fitzpatrick, Cella, Harper & Scinto

(57) ABSTRACT

There is provided an ICG-loaded polymer nanoparticle that is dynamically stable, prevents the leakage of contained ICG and the resulting discoloration, and has a high molar absorbance coefficient. The particle contains a hydrophilic dye (Continued)

having a sulfonate group and a hydrophobic polymer, and the particle further contains at least one of a lipid having a positively charged region, a nicotinic acid derivative and a thiamine derivative.

20 Claims, 9 Drawing Sheets

(51) Int. Cl.
 *A61K 9/51* (2006.01)
 *A61K 49/22* (2006.01)
 *B82Y 15/00* (2011.01)
 *B82Y 30/00* (2011.01)
(52) U.S. Cl.
 CPC ........ *A61K 49/0052* (2013.01); *A61K 49/225* (2013.01); *B82Y 15/00* (2013.01); *B82Y 30/00* (2013.01)

(56) References Cited

U.S. PATENT DOCUMENTS

| | | | |
|---|---|---|---|
| 2011/0104056 A1 | 5/2011 | Hara et al. | |
| 2011/0268775 A1* | 11/2011 | Holt | A61K 9/145 |
| | | | 424/400 |
| 2012/0052011 A1 | 3/2012 | Fukui et al. | |
| 2012/0052017 A1 | 3/2012 | Kato et al. | |
| 2012/0070375 A1 | 3/2012 | Tabata et al. | |

FOREIGN PATENT DOCUMENTS

| | | |
|---|---|---|
| WO | 2009/074274 A1 | 6/2009 |
| WO | 2009/148121 A1 | 12/2009 |
| WO | 2010/018216 A2 | 2/2010 |

OTHER PUBLICATIONS

Victoria B. Rodriguez et al., "Encapsulation and Stabilization of Indocyanine Green Within Poly(styrene-alt-maleic anhydride) Blockpoly(styrene) Micelles for Near-Infrared Imaging," 13(1) J. Biomed. Opt. 014025-1-014025-10 (Jan./Feb. 2008) (XP002664215).
Yong Taik Lim et al., "Biocompatible Polymer-Nanoparticle-Based Bimodal Imaging Contrast Agents for the Labeling and Tracking of Dendritic Cells," 4(10) Small 1640-1645 (Oct. 2008) (XP002664565).
Jie Yu et al., "Synthesis of Near-Infrared-Absorbing Nanoparticle-Assembled Capsules," 19(6) Chem. Mater. 1277-1284 (Feb. 2007) (XP002664566).
U.S. Appl. No. 13/770,536, filed Feb. 19, 2013.

* cited by examiner

SEQUENCE LISTING

```
<160> NUMBER OF SEQ ID NOS: 2

<210> SEQ ID NO 1
<211> LENGTH: 739
<212> TYPE: DNA
<213> ORGANISM: Artificial Sequence
<220> FEATURE:
<223> OTHER INFORMATION: hu4D5-8scFv

<400> SEQUENCE: 1
ccatggatat ccagatgacc cagtccccga gctccctgtc cgcctctgtg ggcgataggg      60
tcaccatcac ctgccgtgcc agtcaggatg tgaatactgc tgtagcctgg tatcaacaga     120
aaccaggaaa agctccgaaa ctactgattt actcggcatc cttcctctac tctggagtcc     180
cttctcgctt ctctggatcc agatctggga cggatttcac tctgaccatc agcagtctgc     240
agccggaaga cttcgcaact tattactgtc agcaacatta tactactcct cccacgttcg     300
gacagggtac caaggtggag atcaaaggcg gtggtggcag cggtggcggt ggcagcggcg     360
gtggcggtag cgaggttcag ctggtggagt ctggcggtgg cctggtgcag caggggggct     420
cactccgttt gtcctgtgca gcttctggct tcaacattaa agacacctat atacactggg     480
tgcgtcaggc cccgggtaag ggcctggaat gggttgcaag gatttatcct acgaatggtt     540
atactagata tgccgatagc gtcaagggcc gtttcactat aagcgcagac acatccaaaa     600
acacagccta cctgcagatg aacagcctgc gtgctgagga cactgccgtc tattattgtt     660
ctagatgggg aggggacggc ttctatgcta tggactactg gggtcaagga accctggtca     720
ccgtctcctc ggcggccgc                                                  739

<210> SEQ ID NO 2
<211> LENGTH: 256
<212> TYPE: PRT
<213> ORGANISM: Artificial Sequence
<220> FEATURE:
<223> OTHER INFORMATION: hu4D5-8scFv

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Gly Gly Gly Gly Ser
            100                 105                 110
Gly Gly Gly Gly Ser Gly Gly Gly Ser Glu Val Gln Leu Val Glu
            115                 120                 125
Ser Gly Gly Gly Leu Val Gln Pro Gly Gly Ser Leu Arg Leu Ser Cys
    130                 135                 140
Ala Ala Ser Gly Phe Asn Ile Lys Asp Thr Tyr Ile His Trp Val Arg
145                 150                 155                 160
Gln Ala Pro Gly Lys Gly Leu Glu Trp Val Ala Arg Ile Tyr Pro Thr
                165                 170                 175
Asn Gly Tyr Thr Arg Tyr Ala Asp Ser Val Lys Gly Arg Phe Thr Ile
                180                 185                 190
Ser Ala Asp Thr Ser Lys Asn Thr Ala Tyr Leu Gln Met Asn Ser Leu
                195                 200                 205
Arg Ala Glu Asp Thr Ala Val Tyr Tyr Cys Ser Arg Trp Gly Gly Asp
                210                 215                 220
Gly Phe Tyr Ala Met Asp Tyr Trp Gly Gln Gly Thr Leu Val Thr Val
225                 230                 235                 240
Ser Ser Ala Ala Ala Leu Glu His His His His His His Gly Gly Cys
                245                 250                 255
```

PARTICLE AND CONTRAST AGENT HAVING THE PARTICLE

TECHNICAL FIELD

The present invention relates to a particle containing an indocyanine green (ICG) composition and a contrast agent having the particle.

BACKGROUND ART

An photoacoustic tomography (hereinafter may be referred to as PAT) apparatus is known as one of apparatuses for visualizing in-vivo information. In the measurement using a PAT apparatus, a tomographic image can be obtained by, measuring the intensity and the generation time of a photoacoustic signal emitted from a substance (optical absorber) that absorbs the light in an object to be measured when the measured object is irradiated with a light, and computing a distribution of the substance in the object.

Any substance can be used as an optical absorber, so long as the substance absorbs a light and emits an acoustic wave in a living body. For example, a blood vessel, a malignant tumor, or the like in the human body can be used as an optical absorber. In addition, a molecular probe such as indocyanine green (hereinafter may be referred to as ICG) can be introduced into the body and used as a contrast agent. ICG is a safe substance that has been approved to be administered into the body. Since ICG sufficiently absorbs a light in the near-infrared wavelength range, which has little influence on the irradiated human body and is highly permeable to a living body, ICG can be suitably used as a contrast agent in a PAT apparatus.

Furthermore, ICG is characterized by emitting fluorescence when excited by a light in the near-infrared wavelength range. ICG can also be used as a fluorescent contrast agent by utilizing this characteristic.

Meanwhile, due to its high degradability in a water, ICG administered as a contrast agent has a problem that it is difficult to be accumulated at a site for measurement.

As a method for solving this problem, a technique to entrap ICG at a high concentration in a particle has been developed. For example, the Journal of Photochemistry and Photobiology B: Biology, 74 (2004) 29-38 (hereinafter referred to as NPL 1) discloses an ICG-containing poly (lactide-co-glycolide) (PLGA) that is obtained by an emulsification solvent diffusion method using polyvinyl alcohol (PVA) as a surfactant. Furthermore, International Patent Publication WO 2010/018216 (hereinafter referred to as PTL 1) describes a nanoemulsion having an oil phase containing ICG covered with a surfactant.

CITATION LIST

Patent Literature

PTL 1: International Patent Publication WO2010/018216

Non Patent Literature

NPL 1: Journal of Photochemistry and Photobiology B: Biology, 74 (2004) 29-38
NPL 2: Journal of Biomedical Optics 131, 014025, 2008

SUMMARY OF INVENTION

However, the ICG-containing PLGA particle disclosed in NPL 1 and the nanoemulsion disclosed in PTL 1 had such a problem that the molar absorption coefficient decreases with time, resulting in lack of stability in absorption of a light in practical use.

This appears to be because, in the case of the ICG-loaded PLGA particle described in NPL 1, water-soluble ICG is leaked into the surrounding water from the inside of the particle dispersed in water, and hence the molar absorbance coefficient of the particle is decreased over time (particle is discolored). Furthermore, since the core of the nanoemulsion described in PTL 1 is a liquid, the nanoemulsion is dynamically unstable. The absorbance is decreased because of aggregation, association, phase separation, and the like occur over time, which leads to destruction of the particle itself, resulting in the leakage of ICG.

In addition, since a polymer matrix such as PLGA is hydrophobic while ICG has a hydrophilic site, the ICG-loaded PLGA particle described in NPL 1 cannot contain a high concentration of ICG.

The present invention was accomplished under the above-described circumstances. An object of the present invention is to provide an ICG-loaded polymer nanoparticle that is dynamically stable, prevents the leakage of ICG contained therein and the resulting discoloration, and has a high molar absorbance coefficient.

The particle according to the present invention is a particle containing a hydrophilic dye having a sulfonate group and a hydrophobic polymer, wherein the particle further has at least one of a lipid having a positively charged region, a nicotinic acid derivative and a thiamine derivative.

According to the present invention, ICG is resistant to leakage from the inside to the outside of the particle. The present invention can therefore provide a particle containing ICG at a high concentration.

Further features of the present invention will become apparent from the following description of exemplary embodiments with reference to the attached drawings.

DESCRIPTION OF EMBODIMENTS

Figure 1A:
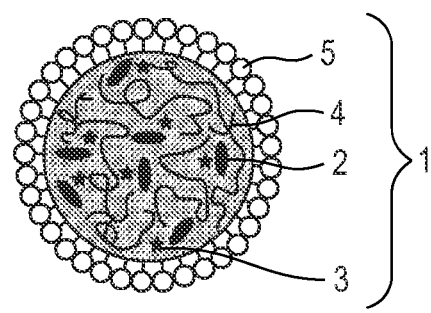
FIGS. 1A, 1B and 1C are schematic views illustrating the structure of the polymer nanoparticle according to the present embodiment.

The embodiments of the present invention will be described in detail below.

The particle according to the present embodiment is a particle having a hydrophilic dye having a sulfonate group and a hydrophobic polymer, wherein the particle further has at least one of a lipid having a positively charged region, a nicotinic acid derivative and a thiamine derivative. In the particle according to the present embodiment, a hydrophobic composition is formed with a hydrophilic dye having a sulfonate group and at least one of a lipid having a positively charged region, a nicotinic acid derivative and a thiamine derivative. Therefore, the particle containing a hydrophobic polymer can contain a hydrophilic dye having a sulfonate group at a high concentration, and can further prevent the leakage of ICG from the inside of the particle and the resulting discoloration. The state that a composition is formed is considered to be a state that a salt is formed by cancelling out the electric charge of a positively charged region of a lipid having a positively charged region, a nicotinic acid derivative or a thiamine derivative and the electric charge of a sulfonate group of a hydrophilic dye having a sulfonate group. Here, since the water-soluble characteristic of a hydrophilic dye having a sulfonate group is attributable to the existence of a sulfonate group, a hydrophobic composition appears to be formed by forming a salt using the sulfonate group as described above. The particle according to the present embodiment can be dynamically stabilized by using a solid polymer as a core.

While the case where a hydrophilic dye having a sulfonate group is ICG will be described below, the dye of the present invention is not limited to ICG. Any of the dyes mentioned in the section of (Hydrophilic dyes having a sulfonate group) below can be used.

The particle according to the present embodiment has indocyanine green and a hydrophobic polymer supporting the indocyanine green, and the particle preferably further has at least one of a lipid having a positively charged region, a nicotinic acid derivative and a thiamine derivative.

In the particle according to the present embodiment, a hydrophobic composition of water-soluble ICG and at least one of a lipid having a positively charged region, a nicotinic acid derivative and a thiamine derivative is formed by adding at least one of a lipid having a positively charged region, a nicotinic acid derivative and a thiamine derivative to the water-soluble ICG. Consequently, ICG can be contained in a particle containing a hydrophobic polymer matrix at a high concentration. Furthermore, the leakage of ICG from the inside of the particle and the resulting discoloration can be prevented.

The state that a composition is formed is considered to be a state that a salt is formed by cancelling out the electric charge of a positively charged region of at least one of a lipid having a positively charged region, a nicotinic acid derivative and a thiamine derivative and the electric charge of a sulfonate group of ICG. Here, since the water-soluble characteristics of ICG is considered to be owing to the existence of a sulfonate group, a hydrophobic composition appears to be formed by forming a salt using the sulfonate group as described above.

<Particles>

First, the particle according to the present embodiment (hereinafter, may be referred to as a polymer nanoparticle) will be described. As illustrated in FIG. 1A, a polymer nanoparticle 1 is a particle that includes a polymer 4 containing indocyanine green (ICG) 2 and an additive 3. The additive 3 is at least one of a lipid having a positively charged region, a nicotinic acid derivative and a thiamine derivative. A surfactant 5 may exist on the surface of this particle.

Figure 1B:
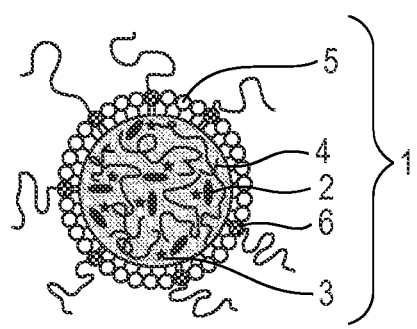

As illustrated in FIG. 1B, the polymer nanoparticle 1 according to another embodiment of the present invention is a particle that has ICG 2 and an additive 3 contained in a polymer 4, wherein two different surfactants 5 and 6 exist on the surface of the particle. At this time, three or more different surfactants may be used.

Figure 1C:
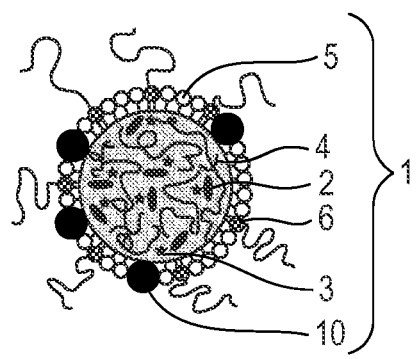

As illustrated in FIG. 1C, the polymer nanoparticle 1 according to yet another embodiment of the present invention is a particle that has ICG 2 and an additive 3 contained in a polymer 4, wherein two different surfactants 5 (surfactant A) and 6 (surfactant B) and albumin 10 exist on the surface of the particle. According to the particle according to this embodiment, leakage of ICG out of the particle can be prevented because albumin on the particle surface is adsorbed to ICG.

The polymer nanoparticle 1 according to yet another embodiment of the present invention is characterized in that a capture molecule is bonded to a part thereof. A target site can be labeled specifically with the capture molecule.

Furthermore, the polymer nanoparticle according to the present embodiments are characterized by containing ICG that absorbs a near-infrared light in a wavelength range between 600 and 900 nm, which has excellent body permeability.

(Particle Size)

Furthermore, the mean particle size of the polymer nanoparticle according to this embodiment can be controlled depending on the purposed use. The mean particle size can be 10 nm or greater and 1,000 nm or smaller. This is because a mean particle size in this range is considered to have an enhanced permeation and retention (EPR) effect. Particles and like are easily leaked from blood vessels in a tumor tissue because a tumor tissue has higher vascular permeability than a normal tissue. These leaked particles further reach the tumor tissue and are accumulated. Such a characteristic of substance accumulation of the tumor tissue is called an EPR effect.

Examples of a method for determining a mean particle size include a method for determining a mean particle size by acquiring a TEM (Transmission Electron Microscope) image and measuring a particle size from the image and a method for determining a mean particle size by using a dynamic light scattering method. Examples of the method for determining a mean particle size by the dynamic light scattering method include a method using a dynamic light scattering analysis apparatus (DLS-8000; Otsuka Electronics Co., Ltd.).

Since ICG is contained in the particle at a high concentration, the polymer nanoparticle according to the present embodiment can have a high molar absorbance coefficient of $1.0 \times 10^8$ $M^{-1}$ $cm^{-1}$ or higher, and can be preferably used as a contrast agent for PAT or a fluorescent contrast agent.

<Hydrophilic Dyes Having a Sulfonate Group>

When the hydrophilic dye having a sulfonate group in the present embodiment is used in the body, a hydrophilic dye, which is easily excreted from the body, is safe and desirable. In the composition according to the present embodiment, it is considered that a lipid having a positively charged region is associated with a sulfonate group and exhibits the effect. Furthermore, a hydrophilic dye preferably absorbs a light in a wavelength range of 600 nm or longer and 1300 nm or shorter called "optical window," which is weakly influenced by absorption and diffusion of a light in the body organism.

Examples of the hydrophilic dye having a sulfonate group include azine dyes, acridine dyes, triphenylmethane dyes, xanthene dyes, porphyrin dyes, cyanine dyes, phthalocyanine dyes, styryl dyes, pyrylium dyes, azo dyes, quinone dyes, tetracycline dyes, flavone dyes, polyene dyes, BODIPY (registered trade name) dyes and indigoid dyes.

Examples of the cyanine dyes include indocyanine green (ICG), Alexa Fluor (registered trade name) dyes (Invitrogen), Cy (registered trade name) dyes (GE Healthcare Biosciences), IR-783, IR-806, IR-820 (Sigma-Aldrich Japan), IRDye 800CW, IRDye 800RS (registered trade name) (LI-COR), ADS780WS, ADS795WS, ADS830WS and ADS832WS (American Dye Source).

(ICG)

In the present embodiment, indocyanine green (ICG) has a structure represented by the following chemical formula 1, or the same composition having a counter ion of $H^+$ or $K^+$ instead of $Na^+$. Furthermore, ICG may contain J-aggregates, having the absorption maximum around 895 nm.

Chemical formula 1

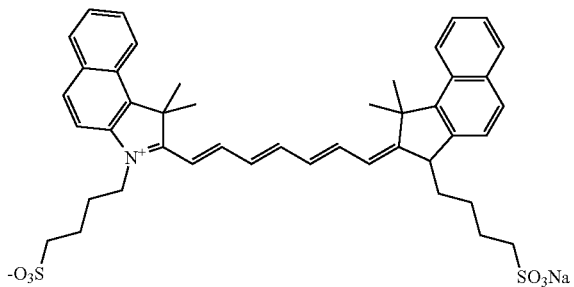

The above-mentioned IR-820 is represented by the following chemical formula 2.

Chemical formula 2

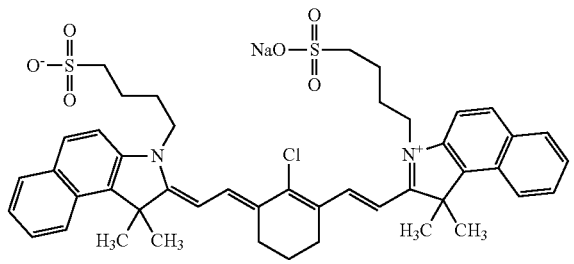

<Additives>

In the present embodiment, the additive is at least one of a lipid having a positively charged region, a nicotinic acid derivative and a thiamine derivative. ICG is a substance having a hydrophilic site. When the additive is added, the positively charged region of the lipid having a positively charged region, the nicotinic acid derivative, or the thiamine derivative is associated with the hydrophilic site (a sulfonate group) of ICG, and hence hydrophobicity of ICG is increased. ICG can be thereby solubilized in an organic solvent, such as chloroform or dichloromethane. ICG may be used as desalted ICG by treatment with a desalting column or the like.

(Lipids Having a Positively Charged Region)

A lipid having a positively charged region refers to a lipid having a partial structure of a cation in a part of the structure thereof. Examples of such a lipid include glycerolipids such as phosphatidylcholine, phosphatidylethanolamine and phosphatidylserine; sphingolipids such as sphingomyelin, sphingophospholipid and sphingosine; glycolipids such as glycosphingolipids having an aminosugar moiety, such as neuraminic acid; synthetic cholesterols such as cholesteryl-3β-carboxyamide ethylene-N-hydroxyethylamine and 3([N—N',N'-dimethylaminoethane)-carbamoyl]cholesterol; synthetic lipids such as laurylamine, stearylamine, N-[1-(2,3-dioleyloxy)propyl]-N,N,N-trimethylammonium chloride (DOTMA) and 2,3-dioleyloxy-N-[2(sperminecarboxyamide)ethyl]-N,N-dimethyl-1-propaniminium trifluoroacetate (DOSPA); and ether-type phospholipids and cationic lipids.

Examples of phosphatidylcholine, phosphatidylethanolamine and phosphatidylserine include diacylphosphatidylcholine, diacylphosphatidylethanolamine and diacylphosphatidylserine.

Furthermore, a lipid having a positively charged region preferably further has a phosphodiester bond. Examples of such a lipid include 1,2-Distearoyl-sn-glycero-3-phosphoethanolamine (DSPE), 1,2-Dipalmitoyl-sn-glycero-3-phosphoethanolamine (DPPE), 1,2-Dimyristoyl-sn-glycero-3-phosphoethanolamine (DMPE), 1,2-Dilauroyl-sn-glycero-3-phosphoethanolamine (DLPE), 1,2-Dioleoyl-sn-glycero-3-phosphoethanolamine (DOPE), 1,2-Dilinoleoyl-sn-glycero-3-phosphoethanolamine (DLoPE), 1,2-Dierucoyl-sn-glycero-3-phosphoethanolamine (DEPE), 1,2-Distearoyl-sn-glycero-3-phospho-L-serine (DSPS), 1,2-Dipalmitoyl-sn-glycero-3-phospho-L-serine (DPPS), 1,2-Dimyristoyl-sn-glycero-3-phospho-L-serine (DMPS), 1,2-Dioleoyl-sn-glycero-3-phospho-L-serine (DOPS), 1,2-Distearoyl-sn-glycero-3-phosphocholine (DSPC), 1,2-Dipalmitoyl-sn-glycero-3-phosphocholine (DPPC), 1,2-Dimyristoyl-sn-glycero-3-phosphocholine (DMPC), 1,2-Dilauroyl-sn-glycero-3-phosphocholine (DLPC), 1,2-Dioleoyl-sn-glycero-3-phosphocholine (DOPC), 1,2-Dilinoleoyl-sn-glycero-3-phosphocholine (DLoPC).

In addition, 1,2-di-o-acyl-sn-glycero-3-phosphocholine, 1,2-diacyl-3-trimethylammoniumpropane chloride, o,o'-ditetradecanoyl-N-(α-trimethylammonioacetyl)diethanolamine chloride or the like can be used as the lipid having a positively charged region in the present embodiment.

The lipid having a positively charged region according to the present embodiment is particularly preferably at least one of dioleylphosphatidylethanolamine and distearoylphosphatidylcholine.

The particle according to the present embodiment may have any one of the above-mentioned lipids having a positively charged region or two or more thereof.

(Nicotinic Acid Derivatives)

The nicotinic acid derivative in the present embodiment is not particularly limited so long as the nicotinic acid derivative has a nicotinic acid skeleton and is preferably represented by the following formula (I):

  (I)

(in the formula (I), A represents one of formulae (a1), (a2) and (a3) below, and
Z represents one of formulae (z1), (z2) and (z3) below)

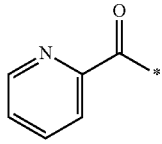
(a1)

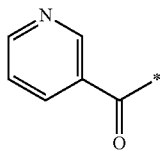
(a2)

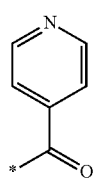
(a3)

(in the formulae (a1), (a2) and (a3), * represents a bonding hand bound to Z of formula (I))

*—NH$_2$ (z1)

*—OR$_1$ (z2)

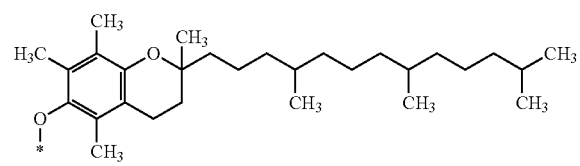
(z3)

(in the formulae (z1), (z2) and (z3), * represents a bonding hand bound to A of formula (I),
in the formula (z2), R$_1$ is one of a hydrogen atom, a substituted or unsubstituted alkyl group having 1 to 10 carbon atoms and a benzyl group, and
the substituent is one of a halogen atom, an alkyl group having 1 to 5 carbon atoms, a hydroxyl group and an amino acid).

When the nicotinic acid derivative in the present embodiment is represented by the above formula (I), positively charged NH$^+$ formed by the nitrogen atom of the pyridine ring and proton existing in the solvent counteracts against the negatively charged sulfonate group of the hydrophilic dye having sulfonate group, to thereby cancel each other's electric charge and to thereby facilitate the solubility of the hydrophilic dye in the hydrophobic solvent. Therefore, irrespective of whether the —CONH$_2$ or the —COR$_1$ is in any of the ortho, meta and para positions, the hydrophilic dye having the nicotinic acid derivative represented by the above formula (I) and the sulfonate group, compared to a single body of the hydrophilic dye, has a high solubility to the hydrophobic solvent.

Examples of the nicotinic acid derivative in the present embodiment include nicotinamide, benzyl nicotinate, nicotinic acid, methyl nicotinate, ethyl nicotinate, ethyl isonicotinate and tocopherol nicotinate. Of these, the nicotinic acid derivative is preferably at least one of nicotinamide and benzyl nicotinate.

The nicotinic acid derivatives may be used solely or as any mixture thereof.

(Thiamine Derivatives)

The thiamine derivative in the present embodiment is not particularly limited and is preferably represented by the following formula (II):

X—B—Y (II)

(in the formula (II), B represents the formula (b) below,
X represents one of formulae (x1), (x2), (x3) and (x4) below, and
Y represents one of formulae (y1) and (y2) below)

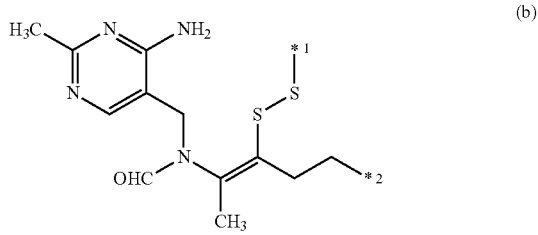 [SMILES: *CC/C(SS*)=C(\C)N(C=O)Cc1cnc(C)nc1N]
(b)

(in the formula (b), *1 represents a bonding hand bound to X of the formula (II), *2 represents a bonding hand bound to Y of the formula (II))

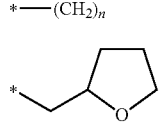
*—(CH$_2$)$_n$ (x1)

(x2)

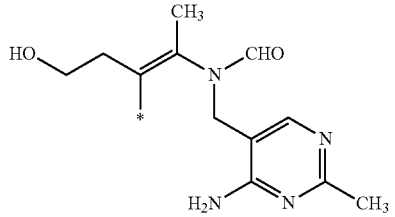
(x3)

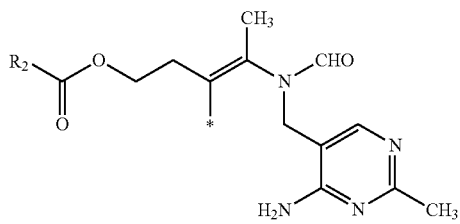
(x4)

(in the formulae (x1), (x2), (x3) and (x4), * represents a bonding hand bound to B of formula (II), in the formula (x1), n is an integer selected from 1 to 10,
the formula (x1) may be substituted by a halogen atom, an alkyl group having 1 to 5 carbon atoms, a hydroxyl group and an amino acid,
in the formula (x4), R$_2$ is one of a substituted or unsubstituted alkyl group having 1 to 10 carbon atoms and a substituted or unsubstituted benzene)

*—OH  (y1)

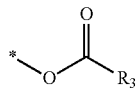  (y2)

(in the formulae (y1) and (y2), * represents a bonding hand bound to B of formula (II),
in the formula (y2), $R_3$ is one of a substituted or unsubstituted alkyl group having 1 to 10 carbon atoms and a substituted or unsubstituted benzene).

Examples of the thiamine derivative include thiamine disulfide, prosultiamine, fursultiamine, bisbentiamine and sulbutiamine. Of these, the thiamine derivative is preferably at least one of fursultiamine, prosultiamine and thiamin disulfide.

The thiamine derivative may be used solely or as any mixture thereof.

The particle according to the present embodiment may have at least one of a lipid having a positively charged region, a nicotinic acid derivative and a thiamine derivative or may have two or more thereof.

(Other Additives)

The particle according to the present embodiment may contain cholesterol.

<Hydrophobic Polymers>

Any hydrophobic polymer can be used in the present embodiment so long as the hydrophobic polymer is a polymer that can contain ICG and the above-described at least one of lipids having a positively charged region, nicotinic acid derivatives and thiamine derivatives. For example, when the polymer nanoparticle in the present embodiment is produced using the nanoemulsion method described later, a polymer that is dissolved in a first liquid 7 to form a nanoemulsion and then is obtained as a solid by distilling off the first liquid 7 may be used. Specific examples include homopolymers of a hydroxycarboxylic acid having six or less carbon atoms, copolymers of two different hydroxycarboxylic acids having six or less carbon atoms, poly(lactide-co-glycolide) copolymers (hereinafter, may be referred to as PLGA), polylactic acid (hereinafter, may be referred to as PLA), poly-L-lactic acid (hereinafter, may be referred to as PLLA), poly-D-lactic acid (hereinafter, may be referred to as PDLA), polystyrene (hereinafter, may be referred to as PS) and polymethylmethacrylate. The average molecular weight of these polymers is preferably 2000 or higher and 1,000,000 or lower, more preferably 10,000 or higher and 600,000 or lower. Ratio between lactic acid and glycolide of the PLGA can be between 10:90 and 90:10, and further can be between 50:50 and 75:25. The particle may contain only one kind of the hydrophobic polymers, or can have more than two kinds of the hydrophobic polymers.

<Surfactants>

The surfactants in the present embodiment (the surfactants 5 [surfactant A] and 6 [surfactant B] in FIGS. 1A, 1B and 1C) are not particularly limited so long as an emulsion of a polymer nanoparticle can be formed. For example, a nonionic surfactant, an anionic surfactant, a cationic surfactant, a polymer surfactant, a phospholipid or the like can be used. One of these surfactants may be used, or two or more thereof may be used.

Examples of the nonionic surfactant used as the above-mentioned surfactant in the present embodiment include polyoxyethylene sorbitan fatty acid esters such as Tween20, Tween40, Tween60, Tween80 and Tween85, Brij35, Brij58, Brij76, Brij98, Triton X-100, Triton X-114, Triton X-305, Triton N-101, Nonidet P-40, Igepol CO530, Igepol CO630, Igepol CO720 and Igepol CO730.

Examples of the anionic surfactant used as the above-mentioned surfactant in the present embodiment include sodium dodecyl sulfate, dodecylbenzene sulfonate, decylbenzene sulfonate, undecylbenzene sulfonate, tridecylbenzene sulfonate, nonylbenzene sulfonate and sodium, potassium and ammonium salts thereof.

Examples of the cationic surfactant used as the above-mentioned surfactant in the present embodiment include cetyltrimethylammonium bromide, hexadecylpyridinium chloride, dodecyltrimethylammonium chloride and hexadecyltrimethylammonium chloride.

Examples of the polymer surfactant used as the above-mentioned surfactant in the present embodiment include polyvinyl alcohol, polyoxyethylene polyoxypropylene glycol and gelatin. Examples of commercially available polyoxyethylene polyoxypropylene glycol include Pluronic F68 (Sigma-Aldrich Japan) and Pluronic F127 (Sigma-Aldrich Japan).

The phospholipid used as the above-mentioned surfactant in the present embodiment is preferably a phosphatidyl phospholipid having any functional group selected from the group consisting of a hydroxyl group, a methoxy group, amino group, a carboxyl group, an N-hydroxysuccinimide group and a maleimide group. Furthermore, a phospholipid used as a surfactant may contain a polyethylene glycol (PEG) chain.

Examples of the phospholipid used as a surfactant that has a functional group selected from the group consisting of a hydroxyl group, a methoxy group, an amino group, an N-hydroxysuccinimide group and a maleimide group and contains a PEG chain include phospholipids represented by the chemical formula 3, such as 1,2-Distearoyl-sn-glycero-3-phosphoethanolamine-N-[poly(ethylene glycol)] (DSPE-PEG-OH), represented by the chemical formula 4, Poly(oxy-1,2-ethanediyl),α-[7-hydroxy-7-oxido-13-oxo-10-[(1-oxooctadecyl)oxy]-6,8,12-trioxa-3-aza-7-phosphatriacont-1-yl]-ω-methoxy-(DSPE-PEG-OMe), represented by the chemical formula 5, N-(aminopropyl polyethyleneglycol)-carbamyl distearoylphosphatidyl-ethanolamine (DSPE-PEG-NH2), represented by the chemical formula 6,3-(N-succinimidyloxyglutaryl)aminopropyl polyethyleneglycol-carbamyl distearoylphosphatidyl-ethanolamine (DSPE-PEG-NHS), represented by the chemical formula 7, N-(3-maleimide-1-oxopropyl)aminopropyl polyethyleneglycol-carbamyl distearoylphosphatidyl-ethanolamine (DSPE-PEG-MAL), dipalmitoylphosphatidyl-ethanolamine containing PEG chain (DPPE-PEG). In the chemical formulas 3 to 7, n is an integer of 5 or more and 500 or less.

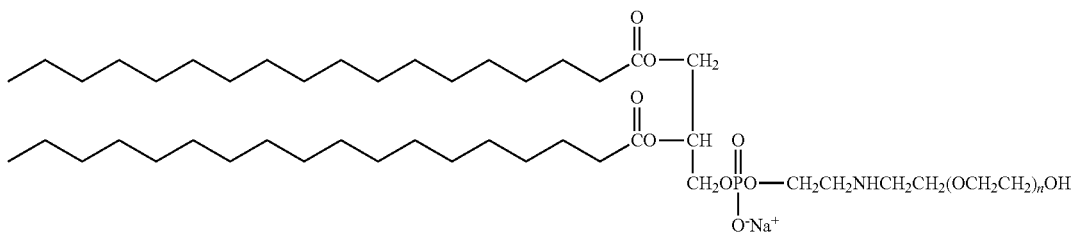

Formula 3

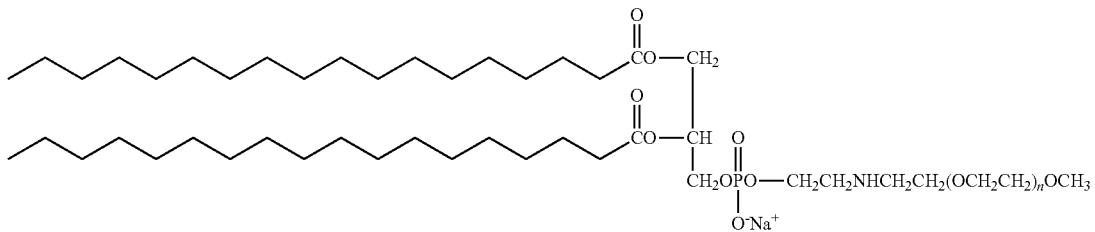

Formula 4

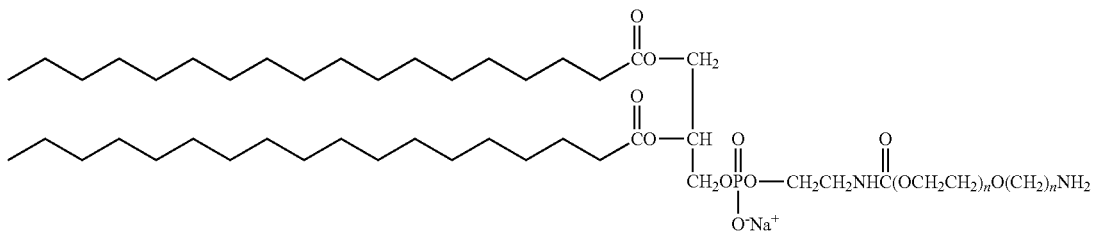

Formula 5

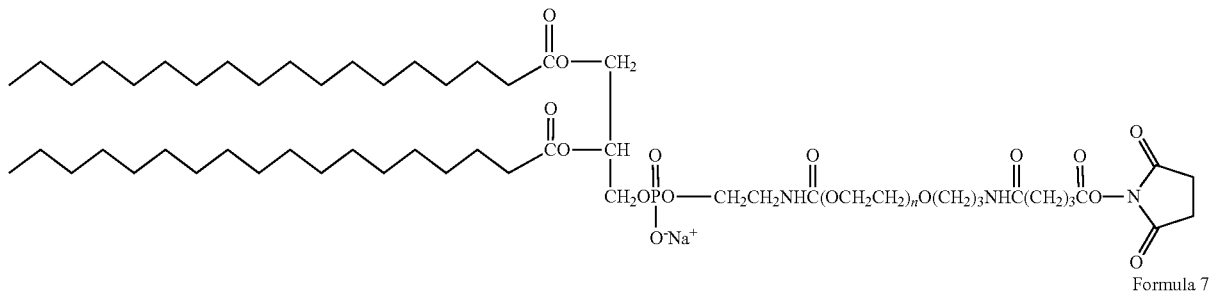

Formula 6

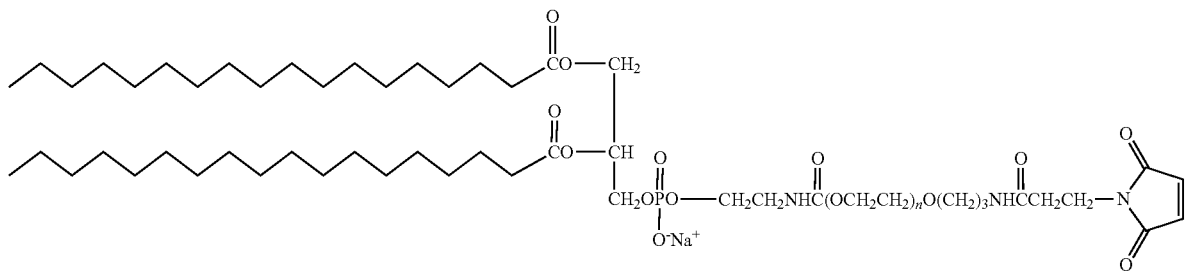

Formula 7

<Albumin>

When the albumin in the present embodiment is administered to a human, human-derived serum albumin is preferred. Serum albumin is a protein having a molecular weight of approximately 67 kDa that is abundant in blood.

<Method for Immobilizing Albumin on the Particle Surface>

The method of immobilizing albumin on the particle surface in the present embodiment mainly involves a force by a noncovalent bond, such as a hydrophobic interaction between albumin and a hydrophobic polymer. Advantages of a noncovalent bond include that the introduction of a functional group for a covalent bond, such as an $NH_2$ group or an SH group, on the particle surface is unnecessary, and hence that labor of preparation can be reduced, that changes in particle properties resulting from changes in the state of an electric charge on the particle surface due to introduction of a functional group can be avoided, and that denaturation of albumin can be avoided. As a noncovalent bond, an ion interaction, a hydrogen bond, van der Waals' force or the like can be used as well as a hydrophobic interaction.

<Method for Producing Polymer Nanoparticle>

The method for obtaining a polymer nanoparticle is not limited, and examples thereof include the nanoemulsion method.

Figure 2:
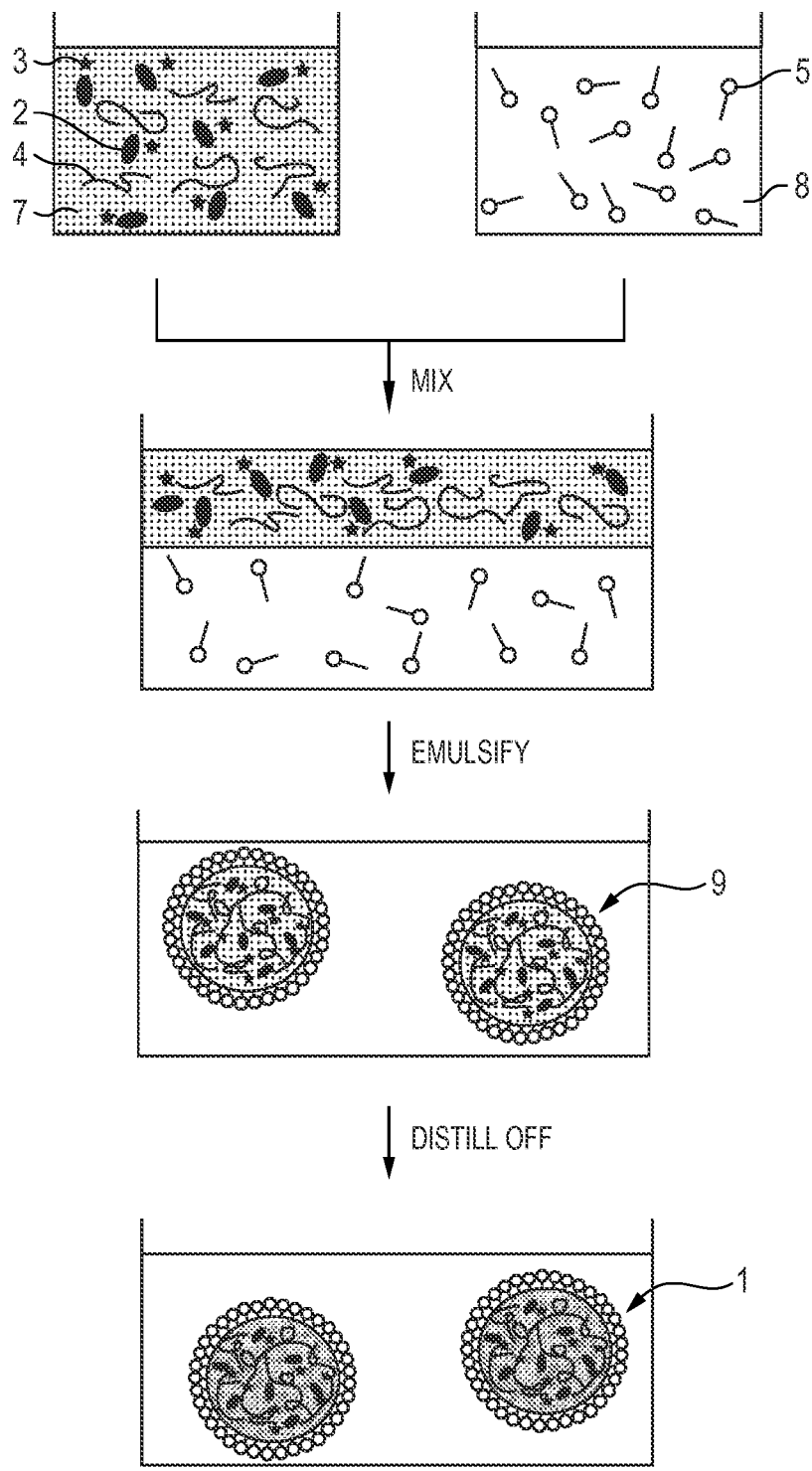
FIG. 2 illustrates an example of steps of producing the polymer nanoparticle according to the present embodiment.

An example of the steps of producing a polymer nanoparticle 1 illustrated in FIG. 1A by the nanoemulsion method is illustrated in FIG. 2. Specifically, an aqueous dispersion of the polymer nanoparticle 1 illustrated in FIG. 1A can be obtained by the following steps (A) to (C).

(A) A step of obtaining a mixture solution by adding a first liquid 7 obtained by dissolving ICG 2, an additive 3 and a polymer 4 in an organic solvent to a second liquid 8, which is an aqueous solution containing a surfactant 5 dissolved therein.

(B) A step of obtaining an O/W-type emulsion 9 by emulsifying the mixture solution.

(C) A step of distilling off the first liquid 7 from dispersoids of the emulsion 9.

Figure 3:
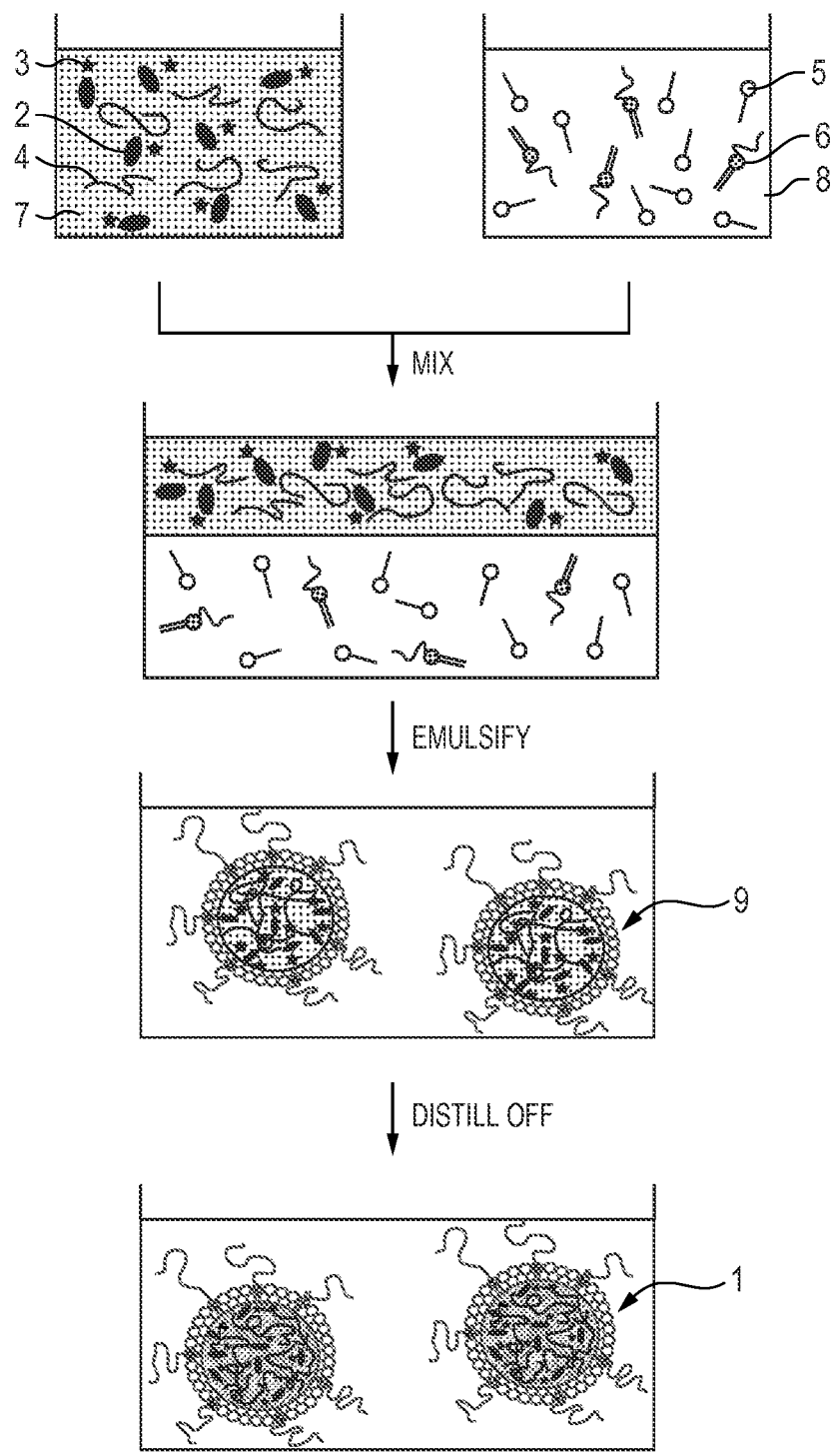
FIG. 3 illustrates another example of steps of producing the polymer nanoparticle according to the present embodiment.

An example of the steps of producing a polymer nanoparticle 1 having two different surfactants illustrated in FIG. 1B is illustrated in FIG. 3. Specifically, an aqueous dispersion of the polymer nanoparticle 1 illustrated in FIG. 1B can be obtained by the following steps (D) to (F). Polymer nanoparticles using three or more different surfactants can also be produced by the same steps.

(D) A step of obtaining a mixture solution by adding a first liquid 7 obtained by dissolving ICG 2, an additive 3 and a polymer 4 in an organic solvent to a second liquid 8, which is an aqueous solution containing surfactants 5 and 6 dissolved therein.

(E) A step of obtaining an O/W-type emulsion 9 by emulsifying the mixture solution.

(F) A step of distilling off the first liquid 7 from dispersoids of the emulsion 9.

Figure 4:
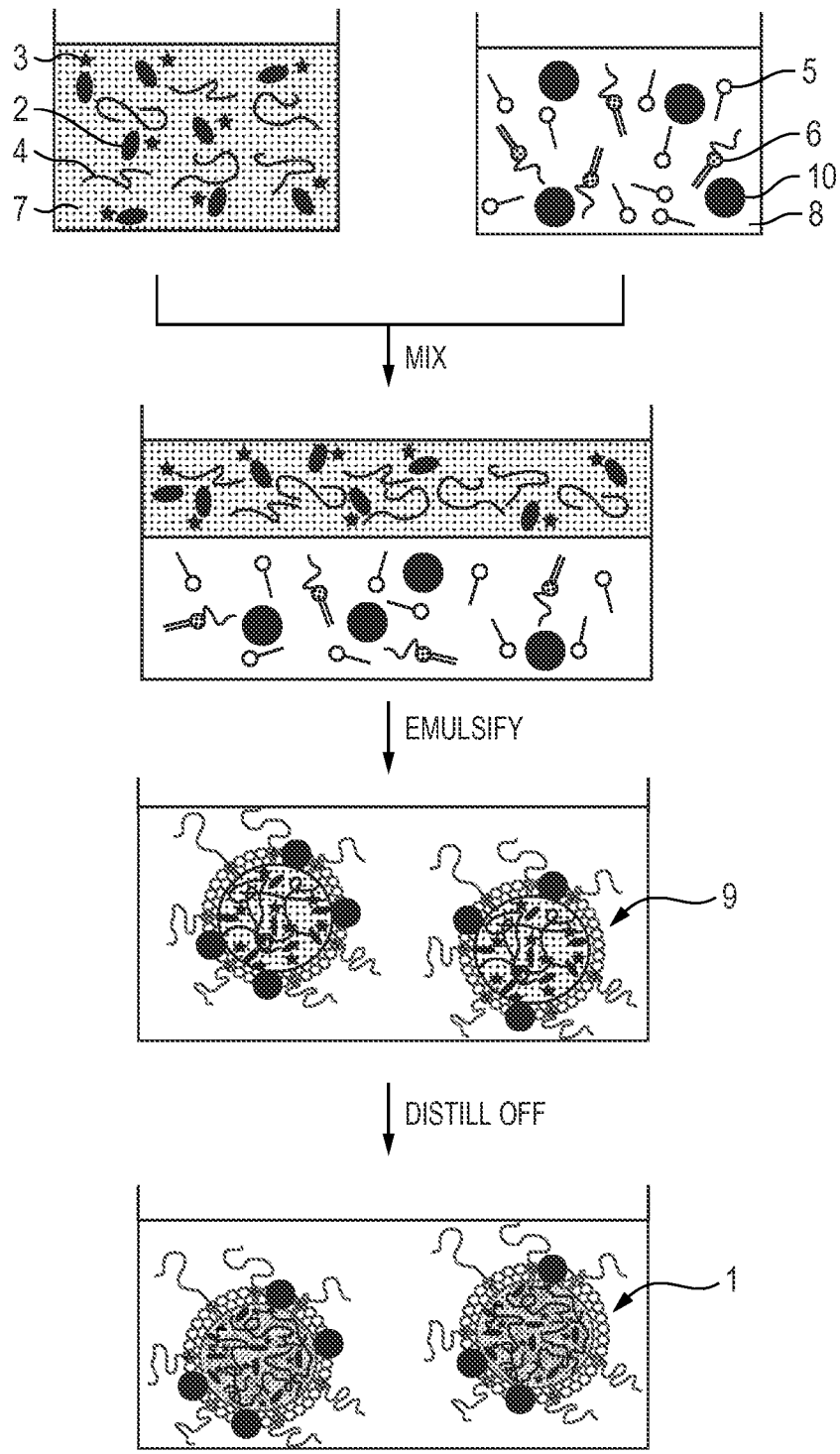
FIG. 4 illustrates yet another example of steps of producing the polymer nanoparticle according to the present embodiment.

An example of the steps of producing a polymer nanoparticle 1 having two different surfactants and albumin illustrated in FIG. 1C is illustrated in FIG. 4. Specifically, an aqueous dispersion of the polymer nanoparticle 1 illustrated in FIG. 1C can be obtained by the following steps (G) to (I).

(G) A step of obtaining a mixture solution by adding a first liquid 7 obtained by dissolving ICG 2, an additive 3 and a polymer 4 in an organic solvent to a second liquid 8, which is an aqueous solution containing surfactants 5 and 6 and albumin 10 dissolved therein.

(H) A step of obtaining an O/W-type emulsion 9 by emulsifying the mixture solution.

(I) A step of distilling off the first liquid 7 from dispersoids of the emulsion 9.

<First Liquid>

Any organic solvent can be used as a solvent of the first liquid 7 used in the above-described nanoemulsion method so long as the organic solvent is insoluble or hardly soluble in water, and a composition including ICG 2 and an additive 3 and a polymer 4 can be dissolved therein. However, a volatile organic solvent is preferred.

Examples of such an organic solvent include, but are not limited to, halogenated hydrocarbons (dichloromethane, chloroform, chloroethane, dichloroethane, trichloroethane, carbon tetrachloride, etc.), ethers (ethyl ether, isobutyl ether, etc.), esters (ethyl acetate, butyl acetate, etc.) and aromatic hydrocarbons (benzene, toluene, xylene, etc.). These organic solvents may be used solely, or two or more thereof can be mixed in suitable proportions.

Furthermore, the concentration of ICG 2 in the first liquid 7 is preferably 0.0005 to 100 mg/mL.

Furthermore, the concentration of polymer 4 in the first liquid 7 is preferably 0.5 to 100 mg/mL.

Furthermore, the weight ratio of ICG 2 and the additive 3 in the first liquid 7 is preferably in the range between 10:1 and 1:20.

Furthermore, the weight ratio of ICG 2 and the polymer 4 in the first liquid 7 is preferably in the range between 1:1 and 1:100.

<Second Liquid>

The second liquid 8 used in the above-described nanoemulsion method is an aqueous solution containing a surfactant 5 (and surfactant 6 and albumin 10) dissolved therein. When the surfactant 5 (and surfactant 6 and albumin 10) is added to the second liquid 8 beforehand, the emulsion can be stabilized when the second liquid 8 is mixed with the first liquid 7. In the present embodiment, however, the surfactant 5 (and surfactant 6 and albumin 10) have only to be contained in a dispersion obtained by mixing the first liquid 7 and the second liquid 8, and the surfactant 5 (and surfactant 6 and albumin 10) does not need to be dissolved in the second liquid beforehand.

Furthermore, the preferred concentration of the surfactant 5 (or surfactant 6 or albumin 10) contained in the second liquid 8 depends on the type of the surfactant and the mixing ratio with the first liquid 7. For example, when a nonionic surfactant, an anionic surfactant, a cationic surfactant or a polymer surfactant is used, the concentration of the surfactant in the second liquid 8 is preferably 0.1 to 100 mg/mL. For example, when a phospholipid containing a PEG chain is used as a surfactant, the concentration of the surfactant in the second liquid 8 is preferably 0.001 to 100 mg/mL.

Furthermore, when a nonionic surfactant, an anionic surfactant, a cationic surfactant or a polymer surfactant is used as the surfactant 5 and a phospholipid containing PEG chain is used as the surfactant 6, the composition ratio of the surfactant 5 and the surfactant 6 is preferably in the range between 100:1 and 1:1 in moles. The ratio of the surfactant 6 exceeding this range is not desirable because formation of a polymer nanoparticle becomes difficult. The ratio of the surfactant 6 lower than this range is not desirable because the number of capture molecules to be immobilized is reduced in immobilization of capture molecules, resulting in the deteriorated labeling performance of the polymer nanoparticle.

(Emulsion)

An emulsion 9 with any physical properties can be used in the above-described nanoemulsion method so long as the emulsion can achieve the object of the present invention. However, the emulsion preferably has a one-peak particle size distribution and an average particle size of 1,000 nm or smaller.

Such an emulsion 9 can be prepared by, for example, an intermittent shaking method, a stirring method using a mixer such as a propeller stirrer or a turbine stirrer, or a known emulsification technique such as a colloid mill method, a homogenizer method or an ultrasonic irradiation method. These methods may be used solely, or two or more thereof can be used in combination. Furthermore, the emulsion 9 may be prepared by single-step emulsification or multiple-step emulsification. However, the emulsification techniques are not limited to these techniques so long as the object of the present invention can be achieved.

The emulsion 9 is an oil-in-water (O/W) type emulsion prepared from a mixture solution obtained by adding the first liquid 7 to the second liquid 8. Here, mixing of the first liquid 7 and the second liquid 8 means to bring the first liquid 7 and the second liquid 8 in contact with each other without being spatially separated. The first liquid 7 and the second liquid 8 do not necessarily mixed with each other.

The proportions of the first liquid 7 and the second liquid 8 in the mixture solution are not particularly limited so long as an oil-in-water (O/W) type emulsion can be formed. However, the first liquid 7 and the second liquid 8 are preferably mixed in a weight ratio in the range between 1:2 and 1:1,000.
(Distilling-Off)

Distilling-off in the above-described nanoemulsion method is a procedure for removing the first liquid 7 from dispersoids of the emulsion 9. Specifically, the first liquid 7 is removed from the dispersoids including ICG 2, an additive 3, a polymer 4 and the first liquid 7 (organic solvent).

Distilling-off can be performed by any known method, and examples thereof include a method of removing a liquid by heating and a method using a pressure reducing apparatus such as an evaporator. When the liquid is removed by heating, the heating temperature is not particularly limited so long as an O/W-type emulsion can be maintained, and the preferred temperature is in the range between 0° C. and 80° C. However, distilling-off is not limited to the above-mentioned techniques so long as the object of the present invention can be achieved.
<Capture Molecules>

In one embodiment of the present invention, a target site can be specifically labeled by immobilizing a capture molecule in a part of the above-mentioned polymer nanoparticle 1.

A capture molecule is a substance that binds specifically to a target site such as a tumor, a substance that binds specifically to a substance existing in an area surrounding a target site, or the like and can be selected from biomolecules and chemical substances such as drugs. Specific examples include antibodies, antibody fragments, enzymes, biologically active peptides, glycopeptides, sugar chains, lipids and molecule recognizing compounds. These substances can be used solely, or two or more thereof can be used in combination.

A target site can be specifically detected, and kinetics, localization, drug efficacy, metabolism and the like of a target substance can be followed by using a polymer nanoparticle 1 having a chemically bonded capture molecule.
<Immobilization of a Capture Molecule>

Any known method of immobilizing a capture molecule on a polymer nanoparticle 1 can be used, although the method depends on the type of the capture molecule, so long as the capture molecule can be chemically bonded to the polymer nanoparticle 1. For example, a method of reacting a functional group of the above-mentioned surfactant 5 or 6 and a functional group of a capture molecule to form a chemical bond and the like can be used.

For example, when the surfactant 5 or 6 is a phosphatidyl phospholipid having an N-hydroxysuccinimide group, a capture molecule can be immobilized on a polymer nanoparticle 1 by reacting with a capture molecule having an amino group. After immobilization of the capture molecule, an unreacted N-hydroxysuccinimide group of the surfactant is preferably inactivated by reacting with glycine, ethanolamine, oligoethylene glycol or polyethylene glycol having an amino group at an end or the like.

When the surfactant 5 or 6 is a phosphatidyl phospholipid having a maleimide group, a capture molecule can be immobilized on a polymer nanoparticle 1 by reacting with a capture molecule having a thiol group. After immobilization of the capture molecule, an unreacted maleimide group of the surfactant is preferably inactivated by reacting with L-cysteine, mercaptoethanol, oligoethylene glycol or polyethylene glycol having a thiol group at an end, or the like.

When the surfactant 5 or 6 is a phosphatidyl phospholipid having an amino group, a capture molecule can be immobilized on a polymer nanoparticle 1 by reacting glutaraldehyde with an amino group of the capture molecule. After immobilization of the capture molecule, the activity of an unreacted amino group is preferably blocked by reacting ethanolamine, oligoethylene glycol or polyethylene glycol having an amino group at an end or the like. Alternatively, a capture molecule may be immobilized by substituting the amino group of the surfactant with an N-hydroxysuccinimide group or a maleimide group.
<Contrast Agent>

The contrast agent according to the present embodiment has the particle according to the present embodiment and a dispersion medium containing the particle dispersed therein.

A dispersion medium is a liquid substance for dispersing the particle according to the present embodiment, and examples thereof include physiological saline and distilled water for injection. To use the contrast agent according to the present embodiment, the above-mentioned particle according to the present embodiment may be dispersed in the dispersion medium beforehand, or the particle according to the present embodiment and the dispersion medium are prepared as a kit, and the particle may be dispersed in the dispersion medium before administered into the body.
<Contrast Agent for Optical Imaging>

In the present embodiment, the term "optical imaging" means imaging by irradiation with a light.

Specifically, an acoustic wave or fluorescence is emitted when a hydrophilic dye having a sulfonate group of the contrast agent for optical imaging according to the present embodiment is irradiated with a light. Photoacoustic imaging can be performed by detecting the emitted acoustic wave. Fluorescence imaging can be performed by detecting the emitted fluorescence. Photoacoustic imaging is a concept including photoacoustic tomography.

The contrast agent for optical imaging according to the present embodiment may further have a dispersion medium such as, for example, physiological saline, distilled water for injection or phosphate-buffered saline (hereinafter, may be referred to as PBS). Furthermore, the contrast agent for optical imaging according to the present embodiment may also have a pharmacologically acceptable additive if necessary.

The contrast agent for optical imaging according to the present embodiment may be dispersed in the above-mentioned dispersion medium beforehand, or may be included in a kit and dispersed in a dispersion medium before administered into the body. Thus, the contrast agent for optical imaging according to the present embodiment can be used as a contrast agent for photoacoustic imaging or a contrast agent for fluorescence imaging.

The contrast agent for optical imaging according to the present embodiment can be accumulated in a larger amount at a tumor site than at a normal site in the body by utilizing the enhanced permeability and retention (EPR) effect when administered into the body. As a result, when the polymer nanoparticle is administered into the body, then the body is irradiated with a light, and an acoustic wave or fluorescence emitted from the body is detected, the acoustic wave or the fluorescence emitted from a tumor site can be made more intense than the acoustic wave or the fluorescence emitted from a normal site. Therefore, the polymer nanoparticle according to the present embodiment can be used as a contrast agent for optical imaging that specifically detects a tumor site.

Furthermore, the polymer nanoparticle according to the present embodiment can target a tumor site by immobilizing the above-described capture molecule.

Since the polymer nanoparticle according to the present embodiment contains ICG, this polymer nanoparticle can absorb wavelengths in the near-infrared wavelength region (wavelength region between 600 and 900 nm), which is safe when delivered to the body and has a relatively high body permeability.

The polymer nanoparticle according to the present embodiment can be used by dispersing the polymer nanoparticle in a solvent such as physiological saline or distilled water for injection. Furthermore, the contrast agent according to the present embodiment may have a pharmacologically acceptable additive, if necessary, in addition to the polymer nanoparticle according to the present embodiment.

<Imaging Method>

A method for detecting the polymer nanoparticle according to the present embodiment with a PAT apparatus after administered into the body will be described below. The method for detecting the polymer nanoparticle according to the present embodiment has the following steps. However, the imaging method according to the present embodiment may include any other steps than the following steps.

(a) A step of administering the polymer nanoparticle according to the present embodiment into the body.

(b) A step of irradiating the body with a light and detecting a photoacoustic signal emitted from the polymer nanoparticle according to the present embodiment existing in the body.

About (a):

The method for administering the polymer nanoparticle according to the present embodiment into the body is not particularly limited, and a method such as oral administration or injection can be employed.

The polymer nanoparticle according to the present embodiment can detect a tumor by the EPR effect even if the polymer nanoparticle does not have a capture molecule.

Furthermore, when a polymer nanoparticle having a capture molecule is used in the body, various target sites can be specifically detected by suitably selecting a capture molecule. For example, when a substance that binds specifically to a tumor is used as a capture molecule, the tumor can be specifically detected. Furthermore, when a substance that binds specifically to a biological substance such as a protein or an enzyme that is abundant in an area surrounding a specific lesion is used as a capture molecule, the lesion can be specifically detected.

About (b):

The light delivered to the body is preferably a near-infrared light having a wavelength between 600 and 900 nm, which is safe when the body is irradiated therewith, and has high body permeability. Furthermore, an apparatus for generating a light and an apparatus for detecting an acoustic signal are not particularly limited, and various apparatuses can be used.

The imaging method using the polymer nanoparticle according to the present embodiment can image a site such as a tumor by the above-described steps (a) and (b)

A method for detecting the particle according to the present embodiment administered into the body with a fluorescence apparatus will be described below. The method for detecting the particle according to the present embodiment has the following steps.

(c) A step of administering the particle according to the present embodiment into the body.

(d) A step of irradiating the body with a light and detecting fluorescence emitted from the particle according to the present embodiment existing in the body.

The method for administering the particle according to the present embodiment into the body in the above step (c) is not particularly limited. Furthermore, in the above step (d), an apparatus for irradiating the body with a light and an apparatus for detecting fluorescence emitted from the particle according to the present embodiment are not particularly limited.

EXAMPLES

The present invention will be described in more detail with reference to the Examples below. However, the scope of the present invention is not limited to these Examples, and materials, composition conditions, reaction conditions and the like can be freely modified so long as a polymer nanoparticle having similar functions and effects can be obtained.

Example 1

Synthesis and Evaluation of Characteristics of Polymer Nanoparticle 1

ICG (5.5 mg, Pharmaceutical and Medical Device Regulatory Science of Japan) was dissolved in 1 mL of methanol to prepare a ICG-methanol solution. Dioleylphosphatidylethanolamine (DOPE) (10.6 mg; NOF Corporation) was dissolved in 2 mL of chloroform to prepare a DOPE-chloroform solution. After 1 mL of the ICG-methanol solution and 2 mL of the DOPE-chloroform solution were mixed, the solvent was distilled off under reduced pressure at 40° C. The ICG and DOPE evaporated to dryness were dissolved in 2 mL of chloroform to prepare an ICG composition 1 containing ICG and DOPE dissolved in chloroform.

5 mg of a poly(lactide-co-glycolide) copolymer (PLGA) (molar ratio of lactic acid and glycolic acid=1:1; molecular weight, 20,000; Wako Pure Chemical Industries, Ltd.) was dissolved in the ICG composition 1 (1.6 mL) to prepare a chloroform solution 1.

Subsequently, the chloroform solution 1 was added to an aqueous solution (20 mL) containing Tween20 (180 mg; Tokyo Kasei Kogyo) and a phospholipid (5% by mole; 22 mg; DSPE-PEG-NH$_2$; molecular weight of PEG, 2,000; NOF Corporation) represented by the chemical formula 5 dissolved therein to prepare a mixture solution, and the mixture solution was stirred. Then, the mixture was treated with an ultrasonic homogenizer for 90 seconds to prepare an O/W-type emulsion.

Subsequently, chloroform was distilled off from dispersoids by reducing pressure of the emulsion with a rotary evaporator (at 40° C. for two hours) to obtain an aqueous dispersion of a polymer nanoparticle 1 having the particle surface protected with Tween20 and a phospholipid and having ICG and DOPE contained in PLGA. Hereinafter, this polymer nanoparticle is referred to as PNP1.

The particle size of PNP1 was analyzed with a dynamic light scattering analyzer (DLS-8000; Otsuka Electronics Co., Ltd.). The average particle size of PNP1 was 84 nm (in terms of weight). The molar absorbance coefficient of PNP1 was $8.0 \times 10^8$ M$^{-1}$cm$^{-1}$. The photoacoustic signal intensity was $1.8 \times 10^9$ VJ$^{-1}$M$^{-1}$.

The photoacoustic signal was measured by irradiating a photoacoustic contrast agent dispersed in water with a pulse laser light, detecting a photoacoustic signal from the contrast agent using a piezoelectric element, amplifying the signal with a high-speed preamplifier, and obtaining a waveform with a digital oscilloscope. Specific conditions are as follows. A titanium sapphire laser (LT-2211-PC; Lotis) was used as a pulse laser light source. The wavelengths used were 710, 750, 800 and 850 nm. The energy density was 20 to 50 mJcm$^{-2}$ (depends on the selected wavelength). The pulse width was approximately 20 ns. The pulse repetition frequency was 10 Hz. A polystyrene cuvette having an optical path length of 1 mm was used as a measurement container for placing the photoacoustic contrast agent dispersed in water. A defocusing-type ultrasonic transducer (V303, Panametrics-NDT) having an element diameter of 1.27 cm and a central band frequency of 1 MHz was used as a piezoelectric element for detecting a photoacoustic signal. The above-mentioned measurement container and the piezoelectric element were placed in a glass container filled with water with a gap of 2.5 cm therebetween. An ultrasonic preamplifier (Model 5682; Olympus Corporation) having 30-dB amplification was used as the high-speed preamplifier for amplifying a photoacoustic signal. The amplified signal was entered in a digital oscilloscope (DPO4104; Tektronix, Inc.). The polystyrene cuvette was irradiated with a pulse laser light from the outside of the glass container. A part of a scattered light generated at this time was detected with a photodiode and entered in a digital oscilloscope as a trigger signal. The digital oscilloscope was set at a mode displaying the average value of 32 measurements to obtain the average photoacoustic signal of 32 laser pulse irradiations.

Example 2

Synthesis and Evaluation of Characteristics of Polymer Nanoparticle 2

DSPC (11.3 mg; NOF Corporation) was used instead of DOPE in Example 1 to prepare an ICG composition 2 containing ICG and DSPC dissolved in chloroform.

The same procedure as in Example 1 was performed using the ICG composition 2 instead of the ICG composition 1 of Example 1 to obtain an aqueous dispersion of a polymer nanoparticle 2 having the particle surface protected with Tween20 and a phospholipid and having ICG and DSPC contained in PLGA. Hereinafter, this polymer nanoparticle is referred to as PNP2.

The average particle size of PNP2 was 70 nm (in terms of weight). The molar absorbance coefficient of PNP2 was $4.7 \times 10^8$ M$^{-1}$cm$^{-1}$. The photoacoustic signal intensity was $9.7 \times 10^8$ VJ$^{-1}$M$^{-1}$.

Example 3

Synthesis and Evaluation of Characteristics of Polymer Nanoparticle 3

DSPC (74.7 mg; NOF Corporation) instead of DOPE in Example 1 and 36.7 mg of ICG were used to prepare an ICG composition 3 containing ICG and DSPC dissolved in chloroform.

The same procedure as in Example 1 was performed using the ICG composition 3 instead of the ICG composition 1 of Example 1 to obtain an aqueous dispersion of a polymer nanoparticle 3 having the particle surface protected with Tween20 and a phospholipid and having ICG and DSPC contained in PLGA. Hereinafter, this polymer nanoparticle is referred to as PNP3.

The average particle size of PNP3 was 166 nm (in terms of weight). The molar absorbance coefficient of PNP3 was $2.8 \times 10^{10}$ M$^{-1}$cm$^{-1}$, and was confirmed to be higher than a known molar absorbance coefficient ($8.6 \times 10^9$) of gold nanorod. Furthermore, the photoacoustic signal of PNP3 was confirmed to be intense, with $9.8 \times 10^{11}$ VJ$^{-1}$M$^{-1}$.

Example 4 (Comparative Example)

Comparison by the Presence or Absence of a Positively Charged Region of a Lipid

Instead of DOPE of Example 1, lipids (chemical formula 8, tristearin; chemical formula 9, triolein; chemical formula 10, ethyl stearate; chemical formula 11, β-carotene; and chemical formula 12, cholesterol acetate) without a positively charged region represented by the following chemical formulas 8 to 12 were used to prepare an ICG composition in the same manner as in Example 1. However, ICG was not dissolved in chloroform in any case, and a target polymer nanoparticle containing ICG could not be obtained.

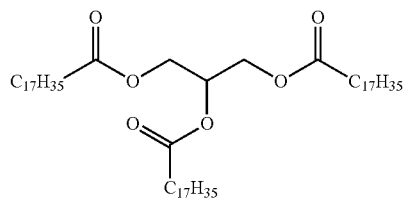

Formula 8

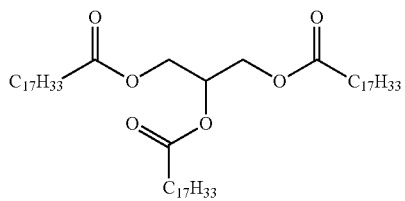

Formula 9

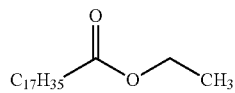

Formula 10

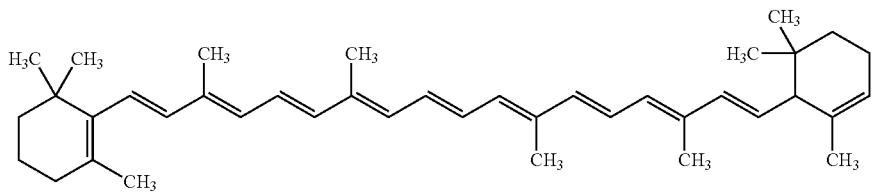

Formula 11

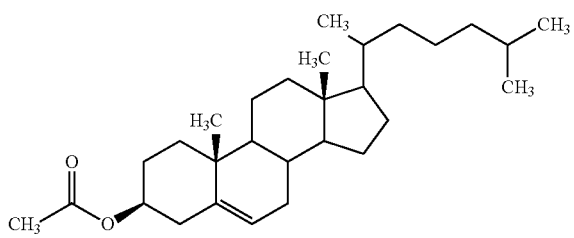

Formula 12

Example 5

Synthesis and Evaluation of Characteristics of Polymer Nanoparticle 4

ICG (5.5 mg) and nicotinamide (17.3 mg; Tokyo Kasei Kogyo) were mixed and dissolved in 2 mL of methanol, and the mixture was stirred for 15 minutes. The solvent was distilled off, then 2 mL of chloroform was added, and the mixture was filtered with a filter having a pore size of 0.45 µm to prepare an ICG composition 4 containing ICG and nicotinamide dissolved in chloroform.

The same procedure as in Example 1 was performed using the ICG composition 4 instead of the ICG composition 1 of Example 1 to obtain an aqueous dispersion of a polymer nanoparticle 4 having the particle surface protected with Tween20 and a phospholipid and having ICG and nicotinamide contained in PLGA. Hereinafter, this polymer nanoparticle is referred to as PNP4.

The average particle size of PNP4 was 73 nm (in terms of weight). The molar absorbance coefficient was $9.1 \times 10^8$ $M^{-1}cm^{-1}$.

Example 6

Synthesis and Evaluation of Characteristics of Polymer Nanoparticle 5

The same procedure as in Example 5 was performed except that the amount of PLGA in Example 5 was increased four-fold (20 mg), to obtain an aqueous dispersion of a polymer nanoparticle 5 having the particle surface protected with Tween20 and a phospholipid and having ICG and nicotinamide contained in PLGA. Hereinafter, this polymer nanoparticle is referred to as PNP5.

The average particle size of PNP5 was 154 nm (in terms of weight). The molar absorbance coefficient was $4.2 \times 10^9$ $M^{-1}cm^{-1}$.

Example 7

Synthesis and Evaluation of Characteristics of Polymer Nanoparticle 6

The same procedure as in Example 5 was performed except that the amount of PLGA was increased eight-fold (40 mg) of the amount used in Example 5, to obtain an aqueous dispersion of a polymer nanoparticle 6 having the particle surface protected with Tween20 and a phospholipid and having ICG and nicotinamide contained in PLGA. Hereinafter, this polymer nanoparticle is referred to as PNP6.

The average particle size of PNP6 was 119 nm (in terms of weight). The molar absorbance coefficient was $2.6 \times 10^9$ $M^{-1}cm^{-1}$.

Example 8

Synthesis and Evaluation of Characteristics of Polymer Nanoparticle 7

The same procedure as in Example 5 was performed by using ICG (22 mg) and nicotinamide (17.3 mg) to prepare an ICG composition 7.

The same procedure as in Example 5 was performed using the ICG composition 7 instead of the ICG composition 4 to obtain an aqueous dispersion of a polymer nanoparticle 7 having the particle surface protected with Tween20 and a phospholipid and having ICG and nicotinamide contained in PLGA. Hereinafter, this polymer nanoparticle is referred to as PNP7.

The average particle size of PNP7 was 76 nm (in terms of weight). The molar absorbance coefficient of PNP7 was $2.5 \times 10^9$ $M^{-1}cm^{-1}$. The photoacoustic signal intensity was $5.7 \times 10^{10}$ $VJ^{-1}M^{-1}$.

Example 9

Evaluation of Stability of Polymer Nanoparticle 1

Figure 5:
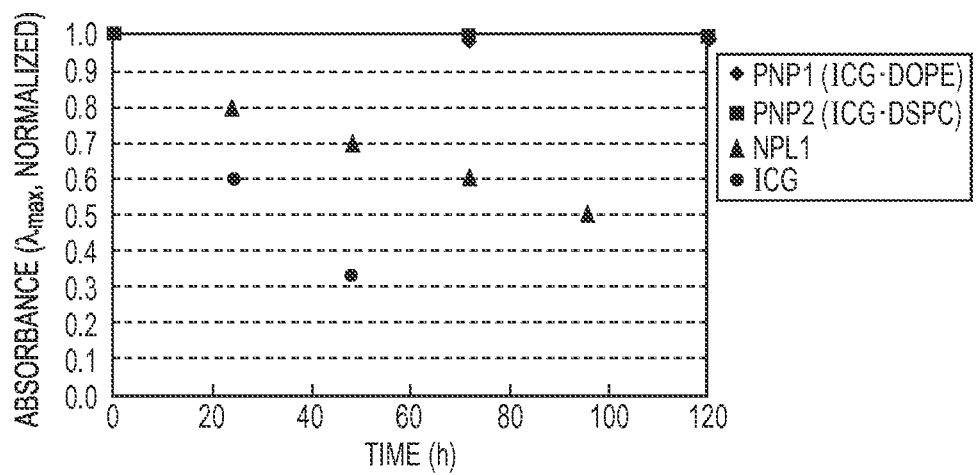
FIG. 5 is a graph illustrating changes with time in the absorbances of PNP1, PNP2, NPL 1 and ICG at $\lambda_{max}$.
Figure 6:
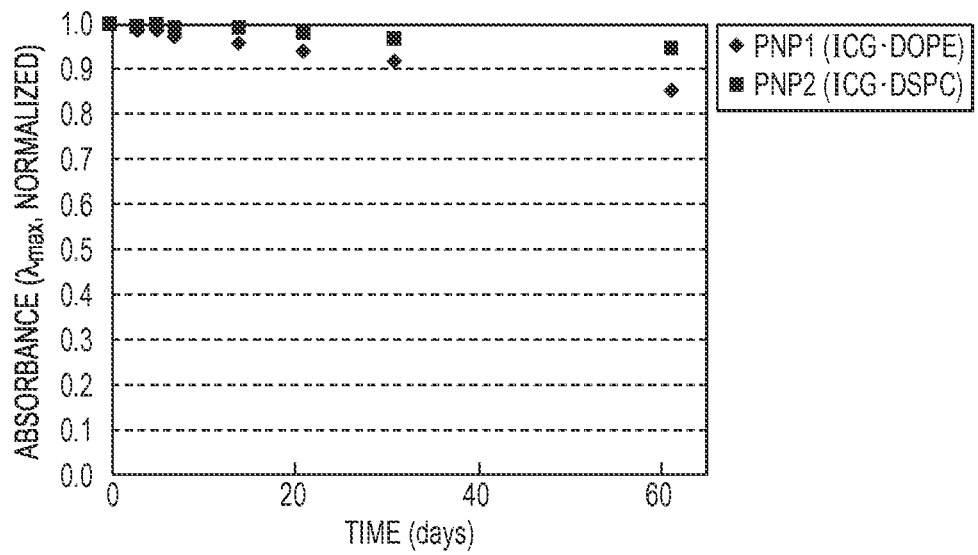
FIG. 6 is a graph illustrating changes with time (over two months) in the absorbances of PNP1 and PNP2 at $\lambda_{max}$.

To evaluate the stability of polymer nanoparticles, aqueous dispersions of PNP1 and PNP2 were allowed to stand at 4° C. in a dark place, and changes in the absorbance at $\lambda_{max}$ were measured over time. The results are illustrated in FIGS. 5 and 6. As a comparative example, changes with time in the absorbance at $\lambda_{max}$ of NPL 1 and in an ICG solution are illustrated in FIG. 5.

As shown in FIG. 5, it was demonstrated that, for five days after the start of measurement, the absorbance change rate of PNP1 was maintained at approximately 1.5%, and the absorbance change rate of PNP2 was maintained at approximately 0.6%. Furthermore, as shown in FIG. 6, it was demonstrated that, even for two months after the start of measurement, the absorbance change rate of PNP1 was maintained at approximately 15%, and the absorbance change rate of PNP2 was maintained approximately 6%. Due to the hydrophobic compositions containing ICG and a lipid having a positively charged region, the leakage of ICG from PNP1 and PNP2 and the resulting discoloration seem to have been prevented. In this and the following Examples, the absorbance change rate refers to a value obtained by dividing an absorbance value at a certain number of days after the start of measurement by the absorbance at the start of measurement.

On the other hand, the absorbance of NPL 1 was decreased to a half in four days, and it was demonstrated that ICG was leaked from the particle resulting in discoloration (FIG. 5). Furthermore, the absorbance change rate of the ICG solution obtained by dissolving ICG in water was 70% at 48 hours, and it was demonstrated that ICG was degraded in water very rapidly, resulting in discoloration.

Example 10

Evaluation of Stability of Polymer Nanoparticle 2

Figure 7:
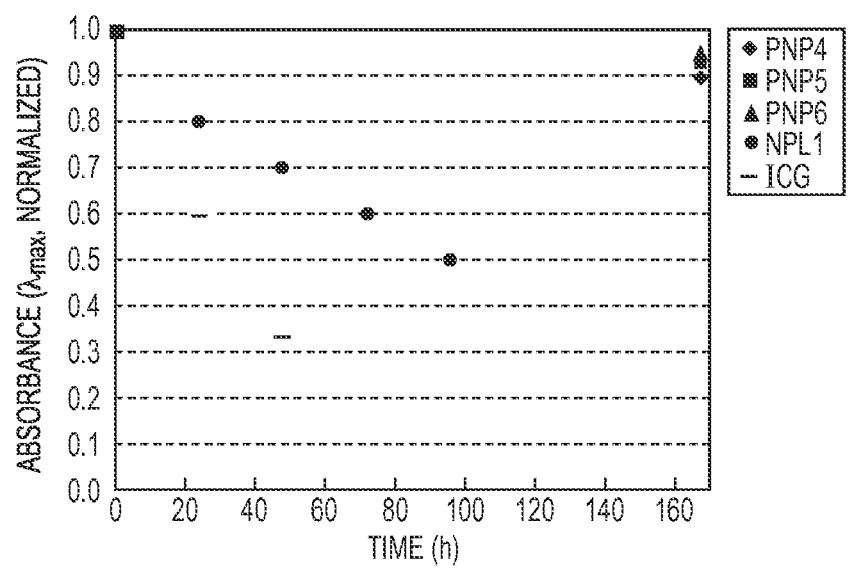
FIG. 7 is a graph illustrating changes with time in the absorbances of PNP4, PNP5, PNP6, NPL 1 and ICG at $\lambda_{max}$.
Figure 8:
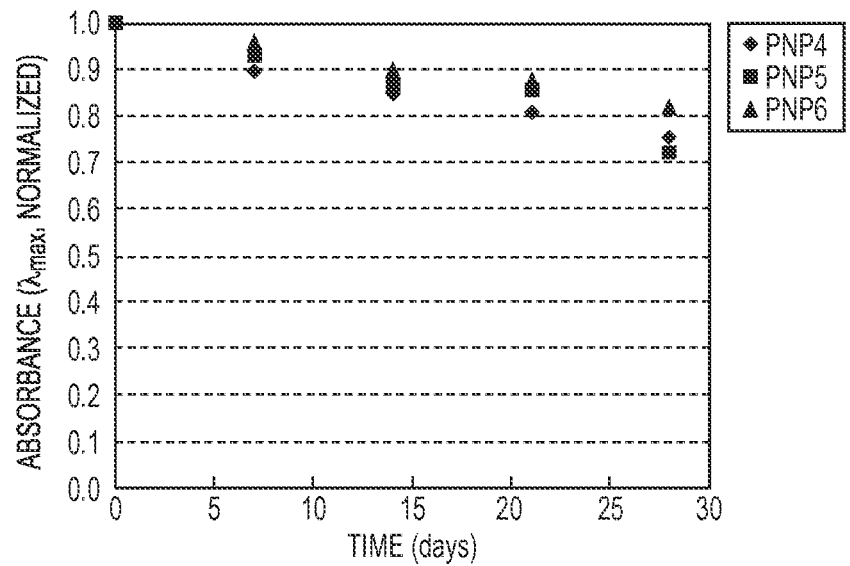
FIG. 8 is a graph illustrating changes with time (over four weeks) in the absorbances of PNP4, PNP5 and PNP6 at $\lambda_{max}$.

Changes in the absorbance of the aqueous dispersions of PNP4 to PNP6 at $\lambda_{max}$ were measured over time in the same manner as in Example 9. The results are illustrated in FIGS. 7 and 8. As a comparative example, changes with time in the absorbance at $\lambda_{max}$ of NPL 1 and in an ICG solution are illustrated in FIG. 7.

As shown in FIG. 7, it was demonstrated that, for seven days after the start of measurement, the absorbance change rate of PNP4 was maintained at approximately 10%, that the absorbance change rate of PNP5 was maintained at approximately 7%, and that the absorbance change rate of PNP6 was maintained at approximately 5%.

Furthermore, as shown in FIG. 8, it was demonstrated that, for four weeks after the start of measurement, the absorbance change rate of PNP4 was maintained at approximately 25%, that the absorbance change rate of PNP5 was maintained at approximately 28%, and that the absorbance change rate of PNP6 was maintained at approximately 18%. Since a PNP has a hydrophobic composition containing ICG and nicotinamide, the leakage of ICG from the PNP and the resulting discoloration seem to have been prevented.

On the other hand, as shown in FIG. 7, the absorbance of NPL 1 had been decreased to a half in four days, and it was demonstrated that ICG was leaked from the particle, resulting in discoloration. Furthermore, the absorbance change rate of the ICG solution was 70% at 48 hours, and it was demonstrated that ICG was degraded in water very rapidly, resulting in discoloration.

Example 11

Synthesis and Evaluation of Characteristics of Polymer Nanoparticle 8

PLGA (5 mg) was dissolved in the ICG composition 2 (1.6 mL) described in Example 2 to prepare a chloroform solution 11.

Subsequently, the chloroform solution 11 (1.6 mL) was added to an aqueous solution (20 mL) obtained by dissolving Tween20 (60 mg) and a phospholipid (7.3 mg; DSPE-020CN; molecular weight of PEG, 2,000; NOF Corporation) in water to obtain a mixture solution, and this mixture solution was stirred. Then, the mixture solution was treated with an ultrasonic homogenizer for 90 seconds with ice cooling to prepare an O/W-type emulsion.

Subsequently, chloroform was distilled off from the emulsion by reducing pressure of the emulsion with a rotary evaporator (40° C., two hours) to obtain an aqueous dispersion of a polymer nanoparticle 8 having the particle surface protected with Tween20 and a phospholipid and having ICG and DSPC contained in PLGA. Hereinafter, this polymer nanoparticle is referred to as PNP8.

Subsequently, an aqueous dispersion of PNP8 was placed in a dialysis membrane (Spectrum Laboratories, Inc.) having a membrane pore of 1,000 kDa and dialyzed against 2 L of water as an extracellular fluid at 4° C. The duration of one dialysis was 16 hours or longer. Dialysis was performed four times. Subsequently, the aqueous dispersion of PNP8 was collected from the dialysis membrane and filtered with a filter having a membrane pore of 0.2 μm.

The average particle size of PNP8 was 83 nm (in terms of weight). The molar absorbance coefficient of PNP8 was $1.5 \times 10^9$ $M^{-1}cm^{-1}$. The photoacoustic signal intensity was $3.5 \times 10^{10}$ $VJ^{-1}M^{-1}$.

Example 12

Synthesis and Evaluation of Characteristics of Polymer Nanoparticle 9

A particle was prepared in the same manner as in Example 11, except that the phospholipid (7.3 mg; DSPE-020CN; molecular weight of PEG, 2,000; NOF Corporation) in Example 11 was not used. As a result, an aqueous dispersion of a polymer nanoparticle 9 having the particle surface protected with Tween20 and having ICG and DSPC contained in PLGA was obtained. Hereinafter, this polymer nanoparticle is referred to as PNP9.

The average particle size of PNP9 was 119 nm (in terms of weight). The molar absorbance coefficient of PNP9 was $5.4 \times 10^9$ $M^{-1}cm^{-1}$. The photoacoustic signal intensity was $1.3 \times 10^{11}$ $VJ^{-1}M^{-1}$.

Example 13

Synthesis and Evaluation of Characteristics of Polymer Nanoparticle 10

A particle was prepared in the same manner as in Example 11, except that a dialysis membrane having a membrane pore of 300 kDa was used instead of the dialysis membrane of Example 11. As a result, an aqueous dispersion of a polymer nanoparticle 10 having the particle surface protected with Tween20 and a phospholipid and having ICG and DSPC contained in PLGA was obtained. Hereinafter, this polymer nanoparticle is referred to as PNP10. The characteristics of PNP10 are shown in Table 1.

Example 14

Synthesis and Evaluation of Characteristics of Polymer Nanoparticle 11

A particle was prepared in the same manner as in Example 11, except that the volume of the chloroform solution 11 in Example 11 was increased approximately two-fold (3.3 mL). As a result, an aqueous dispersion of a polymer nanoparticle 11 having the particle surface protected with Tween20 and a phospholipid and having ICG and DSPC contained in PLGA was obtained. Hereinafter, this polymer nanoparticle is referred to as PNP11. The characteristics of PNP11 are shown in Table 1.

Example 15

Synthesis and Evaluation of Characteristics of Polymer Nanoparticle 12

A particle was prepared in the same manner as in Example 11, except that the volume of the chloroform solution in Example 11 was increased approximately four-fold (6.6 mL). As a result, an aqueous dispersion of a polymer nanoparticle 12 having the particle surface protected with Tween20 and a phospholipid and having ICG and DSPC contained in PLGA was obtained. Hereinafter, this polymer nanoparticle is referred to as PNP12. The characteristics of PNP12 are shown in Table 1.

TABLE 1

|  | Unit | Example 13 (PNP10) | Example 14 (PNP11) | Example 15 (PNP12) |
| --- | --- | --- | --- | --- |
| W/O ratio |  | 20:1.6 | 20:3.3 | 20:6.6 |
| Dry weight | mg/ml | 2.5 | 3.7 | 6.2 |
| Material recovery rate | % | 53 | 62 | 72 |
| Amount of residual chloroform | ppm | Below detection limit (0.5 ppm or less) | Below detection limit (0.5 ppm or less) | Below detection limit (0.5 ppm or less) |
| Average particle size (cumulant) | nm | 134 | 118 | 137 |
| Maximum absorption wavelength | nm | 788 | 786 | 789 |
| ICG content in PNP | % | 4.9 | 6.7 | 7.8 |
| Molar absorbance coefficient | $M^{-1}cm^{-1}$ | $9.8 \times 10^9$ | $8.6 \times 10^9$ | $1.5 \times 10^{10}$ |

Material recovery rate (%) = (dry weight/input material weight) × 100
Amount of residual chloroform: Chloroform was separated by gas chromatography using a headspace and detected with a hydrogen ionization detector.
A PNP having an average particle size of approximately 120 nm was prepared with a W/O ratio in the range between 20:1.6 and 20:6.6. As the W/O ratio is decreased, the material recovery rate and the content of ICG in PNP tended to increase.

Example 16

Synthesis and Evaluation of Characteristics of Polymer Nanoparticle 13

A particle was prepared in the same manner as in Example 11, except that ultrafiltration was performed instead of dialysis purification in Example 11. Specifically, the whole volume of an aqueous dispersion of PNP was placed in a stirred ultrafiltration cell (50 mL, Nihon Millipore k. K.) equipped with an ultrafiltration membrane (membrane pore 300 kDa; Pall Corporation, Japan), and ultrafiltration was performed at room temperature. Ultrafiltration was performed so that water in the same volume as the volume of the waste solution after filtration of the aqueous dispersion of PNP should be newly supplied to the stirred ultrafiltration cell. When the waste solution was obtained in a volume ten times the volume of the aqueous dispersion of PNP, the aqueous dispersion of PNP was collected from the stirred ultrafiltration cell and filtered with a filter having a membrane pore of 0.2 μm to obtain an aqueous dispersion of a polymer nanoparticle 13. Hereinafter, this polymer nanoparticle is referred to as PNP13.

The average particle size of PNP13 was 128 nm (cumulant). The molar absorbance coefficient was $6.8 \times 10^9$ $M^{-1}$ $cm^{-1}$. Similar PNPs were prepared by using either one of a dialysis method and an ultrafiltration method as the method for purifying PNP. The characteristics of these PNPs are shown in Table 2.

Example 17

Synthesis and Evaluation of Characteristics of Polymer Nanoparticle 14

The amounts of ICG and DSPC in Example 11 were increased two-fold, and 1.6 mL of a chloroform solution was prepared. PLGA (5 mg) was dissolved in this solution to prepare a chloroform solution 17.

A polymer nanoparticle 14 was obtained in the same manner as in Example 16 using the chloroform solution 17. Hereinafter, this polymer nanoparticle is referred to as PNP14. The characteristics of PNP14 are shown in Table 2.

Example 18

Synthesis and Evaluation of Characteristics of Polymer Nanoparticle 15

The amounts of ICG, DSPC and PLGA in Example 11 were increased two-fold, and a chloroform solution 18 was prepared. A particle was prepared in the same manner as in Example 16 using this chloroform solution 18. This particle is referred to as PNP15. The characteristics of PNP15 are shown in Table 2.

Example 19

Synthesis and Evaluation of Characteristics of Polymer Nanoparticle 16

The amounts of ICG, DSPC and PLGA in Example 11 were increased four-fold, and a chloroform solution 19 was prepared. A particle was prepared in the same manner as in Example 16 using this chloroform solution. This particle is referred to as PNP16. The characteristics of PNP16 are shown in Table 2.

TABLE 2

|  |  | Unit | Example 16 (PNP13) | Example 17 (PNP14) | Example 18 (PNP15) | Example 19 (PNP16) |
| --- | --- | --- | --- | --- | --- | --- |
| Prescription amount (in multiples) | ICG/DSPC | fold | 1 | 2 | 2 | 4 |
|  | PLGA | fold | 1 | 1 | 2 | 4 |
| Dry weight |  | mg/ml | 1.8 | 3.8 | 4.4 | 7.3 |

TABLE 2-continued

|  | Unit | Example 16 (PNP13) | Example 17 (PNP14) | Example 18 (PNP15) | Example 19 (PNP16) |
|---|---|---|---|---|---|
| Material recovery rate | % | 36 | 66 | 65 | 73 |
| Amount of residual chloroform | ppm | Below detection limit (0.5 ppm or less) | 4 | 2 | 2 |
| Average particle size (cumulant) | nm | 128 | 85 | 98 | 105 |
| Maximum absorption wavelength | nm | 788 | 790 | 789 | 790 |
| ICG CONTENT IN PNP | % | 4.4 | 11.7 | 9.0 | 11.2 |
| Molar absorbance coefficient | $M^{-1}cm^{-1}$ | $6.8 \times 10^9$ | $5.3 \times 10^9$ | $6.4 \times 10^9$ | $9.6 \times 10^9$ |

It was demonstrated that when the prescription amounts of ICG, DSPC and PLGA were increased two-fold or four-fold, PNP having an average particle size of approximately 100 nm could be prepared. Furthermore, the ICG content in PNP could be increased to approximately 10% by increasing the prescription amount of ICG.

Example 20

Evaluation of Stability of Polymer Nanoparticle in Phosphate-Buffered Physiological Saline 0.7 mL of water and 0.1 mL of phosphate-buffered physiological saline (PBS, Invitrogen) having a 10-fold concentration were added to PNP10 (0.2 mL) prepared in Example 13 to prepare a PBS-added PNP dispersion. The average particle size of PNP in the PBS-added PNP dispersion was measured over time for 4 weeks. The dispersion was shielded from a light except when measurement was performed and stored at 4° C. The results are shown in Table 3.

As shown in Table 3, no change was observed in the particle size between immediately after addition of PBS and 4 weeks after addition of PBS, and the particle could be stored in PBS stably.

TABLE 3

| Duration of storage | Average particle size (cumulant) nm |
|---|---|
| Immediately after addition | 82.5 |
| 2 weeks | 84.8 |
| 4 weeks | 83.7 |

Example 21

Evaluation of Stability of Polymer Nanoparticle in 80% Serum 0.8 mL of fetal calf serum (FBS) filtered with a 0.2-μm filter was added to PNP10 (0.2 mL) prepared in Example 13 to prepare an FBS-added PNP dispersion. The average particle size of PNP in the FBS-added PNP dispersion was measured over time for four days. The dispersion was shielded from a light except when measurement was performed and stored at 37° C. The results are shown in Table 4.

As shown in Table 4, no major change was noted in the particle size between 15 minutes after addition of the FBS and 96 hours after addition of the FBS.

TABLE 4

| Duration of storage | Average particle size (cumulant) nm | Polydispersity index |
|---|---|---|
| after 15 min | 134 | 0.25 |
| after 6 h | 124 | 0.26 |
| after 24 h | 125 | 0.26 |
| after 96 h | 101 | 0.28 |

Example 22

Evaluation of Stability of Polymer Nanoparticles

Figure 9:
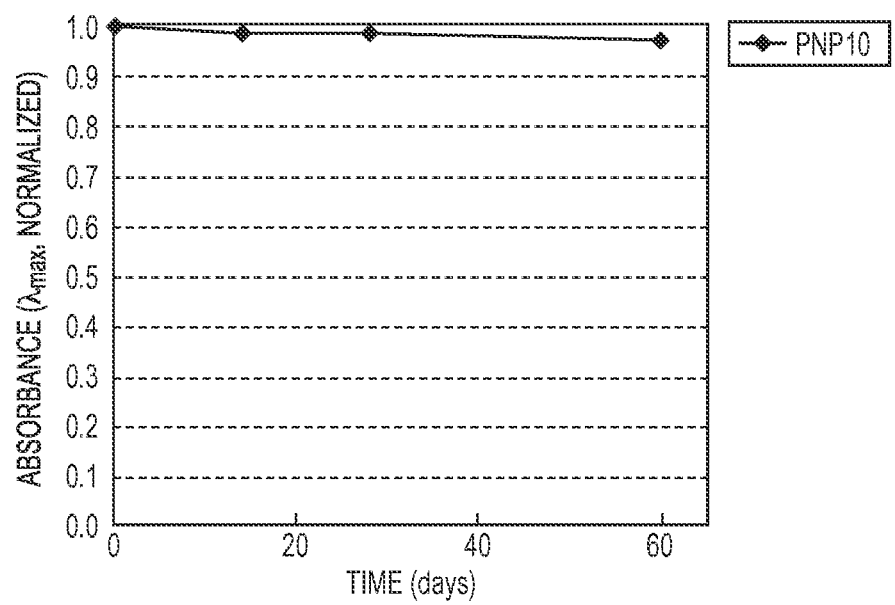
FIG. 9 is a graph illustrating changes with time (over two months) in the absorbance of PNP10 at $\lambda_{max}$.

The PNP10 prepared in Example 13 was diluted with water, and the absorbance was measured over time with an absorption spectrometer (Perkin Elmer). The dispersion was shielded from a light except when measurement was performed and stored at 4° C. The measurement results are illustrated in FIG. 9. As shown in FIG. 9, it was demonstrated that 97% or more absorbance was maintained within two months of storage.

Example 23

Synthesis and Evaluation of Characteristics of Polymer Nanoparticle 17

A particle was synthesized in the same manner as in Example 11, except that the amount of PLGA in Example 11 was increased two-fold. Purification was performed by changing the dialysis membrane to a membrane having a pore size of 300 kDa (Spectrum Laboratories Inc.) to obtain an aqueous dispersion of a polymer nanoparticle 17. Hereinafter, this polymer nanoparticle is referred to as PNP17. The assay results are shown in Table 5.

Example 24

Synthesis and Evaluation of Characteristics of Polymer Nanoparticle 18

A particle was synthesized in the same manner as in Example 11, except that the amount of PLGA in Example 11 was increased four-fold. Purification was performed by changing the dialysis membrane to a membrane having a pore size of 300 kDa to obtain an aqueous dispersion of a polymer nanoparticle 18. Hereinafter, this polymer nanoparticle is referred to as PNP18. The assay results are shown in Table 5.

Example 25

Synthesis and Evaluation of Characteristics of Polymer Nanoparticle 19

A particle was synthesized in the same manner as in Example 11, except that the amount of PLGA in Example 11 was increased eight-fold. Purification was performed by changing the dialysis membrane to a membrane having a pore size of 300 kDa to obtain an aqueous dispersion of a polymer nanoparticle 19. Hereinafter, this polymer nanoparticle is referred to as PNP19. The assay results are shown in Table 5.

TABLE 5

|  | Unit | Example 23 (PNP17) | Example 24 (PNP18) | Example 25 (PNP19) |
|---|---|---|---|---|
| Prescription amount of PLGA | fold | 2 | 4 | 8 |
| Average particle size (cumulant) | nm | 115 | 139 | 179 |
| Maximum absorption wavelength | nm | 790 | 789 | 792 |
| Molar absorbance coefficient | $M^{-1}cm^{-1}$ | $3.3 \times 10^9$ | $3.7 \times 10^9$ | $7.3 \times 10^9$ |
| Normalized PA signal | $VJ^{-1}M^{-1}$ | $5.8 \times 10^{10}$ | $6.0 \times 10^{10}$ | $1.6 \times 10^{11}$ |

It was demonstrated that when the prescription amount of PLGA was increased two-fold, four-fold or eight-fold, particles having a particle size of approximately 100 to 200 nm could be synthesized.

Example 26

Preparation of Single-Stranded Antibody hu4D5-8scFv

A gene hu4D5-8scFv coding for a single-stranded antibody (scFv) was prepared based on the gene sequence (hu4D5-8) of the variable region of IgG that binds to HER2. First, cDNA was prepared by ligating the VL and VH genes of hu4D5-8 with cDNA coding for a peptide (GGGGS)$_3$. The recognition site of a restriction enzyme NcoI- was introduced at the 5' end. The recognition site of a restriction enzyme NotI was introduced at the 3' end. The nucleotide sequence is shown below.

SEQ ID NO: 1:
5'-CCATGGATATCCAGATGACCCAGTCCCCGAGCTCCCTGTCCGCCTC

TGTGGGCGATAGGGTCACCATCACCTGCCGTGCCAGTCAGGATGTGAAT

ACTGCTGTAGCCTGGTATCAACAGAAACCAGGAAAAGCTCCGAAACTAC

TGATTTACTCGGCATCCTTCCTCTACTCTGGAGTCCCTTCTCGCTTCTC

TGGATCCAGATCTGGGACGGATTTCACTCTGACCATCAGCAGTCTGCAG

CCGGAAGACTTCGCAACTTATTACTGTCAGCAACATTATACTACTCCTC

CCACGTTCGGACAGGGTACCAAGGTGGAGATCAAAGGCGGTGGTGGCAG

CGGTGGCGGTGGCAGCGGCGGTGGCGGTAGCGAGGTTCAGCTGGTGGAG

TCTGGCGGTGGCCTGGTGCAGCCAGGGGGCTCACTCCGTTTGTCCTGTG

CAGCTTCTGGCTTCAACATTAAAGACACCTATATACACTGGGTGCGTCA

GGCCCCGGGTAAGGGCCTGGAATGGGTTGCAAGGATTTATCCTACGAAT

GGTTATACTAGATATGCCGATAGCGTCAAGGGCCGTTTCACTATAAGCG

CAGACACATCCAAAAACACAGCCTACCTGCAGATGAACAGCCTGCGTGC

TGAGGACACTGCCGTCTATTATTGTTCTAGATGGGGAGGGGACGGCTTC

TATGCTATGGACTACTGGGGTCAAGGAACCCTGGTCACCGTCTCCTCGG

CGGCCGC-3'

(The recognition sites of the restriction enzymes are underlined).

The above-described gene fragment hu4D5-8scFv was inserted downstream of the T7/lac promoter of a plasmid pET-22b(+) (Novagen). Specifically, the above-described cDNA was ligated to pET-22b(+) digested with the restriction enzymes NcoI- and NotI.

This expression plasmid was transformed into *Escherichia coli* (*Escherichia coli* BL21[DE3]) to obtain a bacterial strain for expression. The obtained bacterial strain was precultured overnight in 4 mL of an LB-Amp medium, and the total amount was added to 250 mL of a 2×YT medium and cultured at 28° C. with shaking at 120 rpm for eight hours. Then, isopropyl-β-D(-)-thiogalactopyranoside (IPTG) was added at a final concentration of 1 mM, and the bacteria were cultured overnight at 28° C. The culture broth of *Escherichia coli* were centrifuged at 8000×g at 4° C. for 30 minutes, and the culture broth supernatant was collected. Ammonium sulfate of 60% weight of the obtained culture broth was added, and proteins were precipitated by salting out. The solution subjected to salting out was allowed to stand overnight at 4° C. and centrifuged at 8000×g at 4° C. for 30 minutes to collect a precipitate. The obtained precipitate was dissolved in 20 mM Tris.HCl/500 mM NaCl buffer, and the mixture was dialyzed against 1 L of the buffer. After the dialysis, the protein solution was added to a column filled with His.Bind (registered trade name) Resin (Novagen) and purified by metal chelate affinity chromatography using an Ni ion. The purified hu4D5-8scFv showed a single band on reduced SDS-PAGE. It was demonstrated that the molecular weight was approximately 28 kDa. The amino acid sequence of the prepared antibody is shown below. Hereinafter, hu4D5-8scFv is referred to as scFv.

SEQ ID NO: 2:
DIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTF

GQGTKVEIKGGGGSGGGGSGGGGSEVQLVESGGGLVQPGGSLRLSCAAS

GFNIKDTYIHWVRQAPGKGLEWVARIYPTNGYTRYADSVKGRFTISADT

SKNTAYLQMNSLRAEDTAVYYCSRWGGDGFYAMDYWGQGTLVTVSSAAA

LEHHHHHHGGC

Example 27

Synthesis of Polymer Nanoparticle 20

ICG (4.4 mg) was dissolved in 1 mL of methanol to prepare an ICG-methanol solution. DSPC (9 mg) was dissolved in 1 mL of chloroform to prepare a DSPC-chloroform solution. 1 mL of the ICG methanol solution and 1 mL of the DSPC chloroform solution were mixed, the mixture was stirred for five minutes, and the solvent was distilled off under reduced pressure at 40° C. ICG and DSPC evaporated to dryness were completely dissolved in 1.6 mL of chloroform, to prepare an ICG composition containing ICG and DSPC dissolved in chloroform. PLGA (20 mg) was dissolved in this composition to prepare a PLGA-chloroform solution. Subsequently, the PLGA-chloroform solution was added to an aqueous solution (20 mL) containing Tween20 (60 mg), N-(carbonyl-methoxypolyethyleneglycol 2000)-1,2-distearoyl-sn-glycero-3-phosphoethanolamine, sodium salt (7.3 mg; DSPE-020CN), which is a polyethyleneglycolated phospholipid having a methoxy group at an end, and N-(aminopropylpolyethyleneglycol)carbamyl-distearoylphosphatidyl-ethanolamine (0.7 mg; DSPE-020PA; NOF Corporation), which is a polyethylene-glycolated phospholipid having a primary amino group at an end, dissolved therein to prepare a mixture solution. This mixture solution was stirred at room temperature for three minutes. Then, the mixture solution was treated with an ultrasonic homogenizer for 90 seconds to prepare an O/W-type emulsion. Subsequently, chloroform was distilled off from the emulsion solution by reducing pressure of the emulsion with a rotary evaporator at 40° C. for two hours. Then, the solution was adequately dialyzed against water, and an aqueous dispersion of a polymer nanoparticle 20 containing ICG and DSPC was obtained by filtration with a filter (pore size, 0.2 μm). This particle is referred to as PNP20.

The average particle size and zeta potential of PNP20 in water were measured using a Zetasizer nano (Malvern Instruments Ltd.). The average particle size of PNP20 was 105 nm (cumulant). The zeta potential was −31 mV.

Example 28

Labeling PNP20 Surface with scFv

The buffer for scFv prepared in Example 26 was replaced with a phosphate buffer (2.68 mM KCl, 137 mM NaCl, 1.47 mM $KH_2PO_4$, 1 mM $Na_2HPO_4$, and 5 mM EDTA; pH 7.4) containing 5 mM EDTA, and the solution was reduced with 10-fold molar quantity of tri(2-carboxyethyl)phosphine hydrochloride (TCEP) at 25° C. for approximately two hours.

scFv was labeled via a primary amino group present on the surface of PNP20. First, 0.1 mg (233 nmol) of succinimidyl-[(N-maleimidopropionamido)-diethyleneglycol]ester $(SM(PEG)_2$; Thermo Fisher Scientific K.K.) was dissolved in 2.9 mL of the aqueous dispersion (PNP concentration, $4.8 \times 10^{12}$/mL) of PNP20. Subsequently, 0.33 mL of a borate buffer (pH 8.5) was added. This particle suspension was stirred at room temperature for two hours, and maleimide group-introduced PNP20 (hereinafter, maleimidated PNP20) and unreacted $SM(PEG)_2$ were separated with a PD-10 desalting column (GE Healthcare Biosciences) using water as a developing solvent to obtain approximately 6 mL of an aqueous solution of maleimidated PNP20. 120 μL of a 1 M 2-[4-(2-hydroxyethyl)-1-piperazinyl]ethanesulfonic acid (HEPES) solution was added to this aqueous solution to obtain a HEPES solution of maleimidated PNP20.

The reduced scFv was added to the HEPES solution of maleimidated PNP20 and reacted at 4° C. for 15 hours. The reaction molar ratio (scFv/maleimidated PNP20) of the charged substances was 720. The term "to charge" used herein means to add to a reaction system. The expression "reaction molar ratio of the charged substances" means a molar concentration ratio of scFv and maleimidated PNP20 added to a reaction system. After reaction, 16.8 nmol of polyethylene glycol (molecular weight, 1,000; PLS-606; Creative PEGWorks) having a thiol group at an end was added to this solution, and the mixture was stirred at room temperature for 30 minutes. Subsequently, this solution was filtered with a filter (pore size, 1.2 μm), scFv molecules that did not bind to maleimidated PNP20 were removed by ultrafiltration with Amicon Ultra-4 having a pore size of 100 kDa (Nihon Millipore K.K.) to obtain scFv-labeled PNP20. Hereinafter, the obtained particle is referred to as scFv-PNP20.

The amount of PNP20 labeled with scFv was measured using the bicinchoninic acid (BCA) method. As a result, it was shown that each particle was labeled with 491 scFv molecules. The average particle size and the zeta potential of scFv-PNP20 in water were measured with Zetasizer nano (Malvern Instruments Ltd.). The average particle size of scFv-PNP20 was 109 nm (cumulant). The zeta potential was −40 mV.

Example 29

Evaluation of Ability of scFv-PNP20 to Bind to Cells

The ability of scFv-PNP20 to bind to cultured cells was evaluated. On the day before, HER2-positive cells (N87 cells) and HER2-negative cells (SUIT-2 cells) were seeded on respective 24-well plates ($4 \times 10^{5}$ cells/well). On the following day, the medium was removed, 200 μL of a growth medium was placed, and scFv-PNP20 was added (PNP concentrations, 0, 16, 33, 81, 157, and 300 μM). The medium was allowed to stand at 4° C. for three hours. Then, the medium containing scFv-PNP20 was removed, and the plates were thoroughly washed twice with 1 mL of PBS. After PBS was removed, 300 μL of 1% aqueous solution of Triton X-100 (polyoxyethylene-p-isooctylphenol) per well was added to lyse cells. The plates were incubated at 37° C. for one hour or longer. This cell lysate was collected, and the amount of ICG in the solution was obtained by fluorometry. Fluorometry was performed with an excitation wavelength of 790 nm and a fluorescence wavelength of 820 nm. A scatchard plot was created with fluorescence intensity and the concentration of incubated scFv-PNP20, and the apparent equilibrium dissociation constant (Kd) of scFv-PNP20 against N87 cells was 0.17 nM. On the other hand, since binding to SUIT-2 cells was weak, and the fluorescence intensity was low as a result, Kd could not be obtained from the scatchard plot. From the above results, it was demonstrated that scFv-PNP20 binds to HER2-positive cells by recognizing HER2.

Example 30

Synthesis and Evaluation of Characteristics of Polymer Nanoparticles 21 to 23

PLGA (20 mg) was dissolved in the ICG composition 2 (1.6 mL) prepared in Example 2 to prepare a chloroform solution 30.

Subsequently, the above-described chloroform solution (1.6 mL) was added to an aqueous solution (20 mL) containing Tween80 (Tokyo Kasei Kogyo) to prepare a mixture solution, and this mixture solution was stirred. Then, this mixture solution was treated with an ultrasonic homogenizer for 90 seconds with ice cooling to prepare an O/W-type emulsion.

Subsequently, chloroform was distilled off from the emulsion by reducing pressure of the emulsion with a rotary evaporator (40° C., two hours) to obtain aqueous dispersions of polymer nanoparticles 21, 22 and 23 having Tween80 on the particle surface and having ICG and DSPC contained in PLGA. Here, the polymer nanoparticles 21, 22 and 23 are particles using aqueous solutions (20 mL) containing 180, 60 and 12 mg, respectively, of Tween80 (Tokyo Kasei Kogyo).

Subsequently, the aqueous dispersion of the polymer nanoparticle 21 was placed in an ultrafiltration apparatus (ultrafiltration membrane having a membrane pore of 300 kDa; Pall Corporation, Japan), ultrafiltration was performed while pouring water until the volume of the waste solution became 400 mL. The same ultrafiltration as for the polymer nanoparticle 21 was performed for the polymer nanoparticles 22 and 23.

Subsequently, the aqueous dispersions (all 20 mL) of polymer nanoparticles 21, 22 and 23 were collected from the ultrafiltration apparatus and filtered with a filter having a membrane pore of 0.2 μm. Hereinafter, these polymer nanoparticles are referred to as PNP21, PNP22 and PNP23. The measurement results of the average particle sizes (cumulant sizes) and the molar absorbance coefficients of PNP21, PNP22 and PNP23 are shown in Table 6.

Example 31

Synthesis and Evaluation of Characteristics of Polymer Nanoparticles 24 to 26

Polymer nanoparticles were prepared in the same manner as in Example 30, except that an aqueous solution containing Pluronic F68 (Sigma-Aldrich Japan) was used instead of the aqueous solution containing Tween80 (Tokyo Kasei Kogyo) in Example 30. Specifically, aqueous dispersions of polymer nanoparticles 24, 25 and 26 having Pluronic F68 (Sigma-Aldrich Japan) on the particle surface and having ICG and DSPC contained in PLGA were obtained. Here, polymer nanoparticle 24, 25 and 26 are particles obtained using aqueous solution (20 mL) containing 268, 100 and 50 mg, respectively, of Pluronic F68 (Sigma-Aldrich Japan). Hereinafter, these polymer nanoparticles are referred to as PNP24, PNP25 and PNP26. The measurement results of the average particle sizes (cumulant sizes) and the molar absorbance coefficients of PNP24, PNP25 and PNP26 are shown in Table 6.

Example 32

Synthesis and Evaluation of Characteristics of Polymer Nanoparticles 27 to 29

Polymer nanoparticles were prepared using an aqueous solution containing Pluronic F127 (Sigma-Aldrich Japan) instead of the aqueous solution containing Tween80 (Tokyo Kasei Kogyo) in Example 30. Specifically, aqueous dispersions of polymer nanoparticles 27, 28 and 29 having Pluronic F127 on the particle surface and having ICG and DSPC in PLGA were obtained. Here, polymer nanoparticles 27, 28 and 29 are particles obtained using aqueous solutions (20 mL) containing 268, 100 and 50 mg, respectively, of Pluronic F127 (Sigma-Aldrich Japan) dissolved therein. Hereinafter, these polymer nanoparticles are referred to as PNP27, PNP28 and PNP29.

The average particle sizes (cumulant sizes) and the molar absorbance coefficients of PNP27, PNP28 and PNP29 are shown in Table 6.

TABLE 6

|  | Unit | Example 30 | | | Example 31 | | | Example 32 | | |
| --- | --- | --- | --- | --- | --- | --- | --- | --- | --- | --- |
|  |  | PNP21 | PNP22 | PNP23 | PNP24 | PNP25 | PNP26 | PNP27 | PNP28 | PNP29 |
| Average particle size | nm | 103 | 149 | 113 | 121 | 103 | 119 | 108 | 110 | 101 |
| Molar absorbance coefficient | $\times 10^9$ $M^{-1}cm^{-1}$ | 1.6 | 14 | 7.9 | 13 | 6.4 | 8.4 | 2.8 | 3.7 | 15 |

The molar absorbance coefficient of PNP2 having the particle surface protected with Tween20 and a phospholipid was $4.7 \times 10^8$ $M^{-1}cm^{-1}$.
PNP21 to PNP29 having particle surface Tween80, Pluronic F68 or Pluronic F68, which were prepared in Examples 30 to 32, had molar absorbance coefficients comparable or superior to that of PNP2.

Example 33

Synthesis and Evaluation of Characteristics of Particles Containing Albumin in the Surface ICG (13.2 mg) was dissolved in 3 mL of methanol to prepare an ICG-methanol solution. DSPC (27 mg) was dissolved in 3 mL of chloroform to prepare a DSPC-chloroform solution. After 3 mL of the ICG methanol solution and 3 mL of the DSPC-chloroform solution were mixed, the solvent was distilled off under reduced pressure at 40° C. ICG and DSPC evaporated to dryness were dissolved in 4.8 mL of chloroform to prepare an ICG composition 33 containing ICG and DOPE dissolved in chloroform.

60 mg of PLGA was dissolved in 4.8 mL of a chloroform solution of the ICG composition 33 to prepare a chloroform solution 33.

Subsequently, an aqueous solution (60 mL) containing Tween20 (180 mg) and a phospholipid (21.9 mg; DSPE-020CN; molecular weight of PEG, 2,000; NOF Corporation) was prepared. An aqueous solution (60 mL) of Tween20 and a phospholipid was divided to 20 mL each, and 0, 5.2 or 52 mg of human serum albumin (Calbiochem) were added to prepare aqueous solutions of Tween20 and a phospholipid containing 0, 5.2 or 52 mg of albumin. 1.6 mL each of the chloroform solution 33 was added to 20 mL of these three different aqueous solutions to prepare mixture solutions, and the mixture solutions were stirred. Then, the mixture solutions were treated with an ultrasonic homogenizer for 90 seconds to prepare O/W-type emulsions. Subsequently, pressure of these emulsions was reduced with a rotary evaporator (at 40° C. for two hours) to distill off chloroform from dispersoids. As a result, aqueous dispersions of particles having particle surface protected with Tween20 and phospholipid and having ICG and DSPC contained in PLGA were obtained in the system not using albumin. Aqueous dispersions of particles protected with Tween20, phospholipid and albumin and having ICG and DSPC contained in PLGA were obtained in the system using albumin. Dialysis of the obtained aqueous dispersions against pure water (2 L) was repeated five times, and then ultrafiltration using Amicon Ultra-4 (Nihon Millipore K.K.) having a pore size of 100 kDa was performed to remove substances that did not form a particle and albumin molecules that did not bind to a particle. Finally, filtration with a 0.45-μm filter was performed to obtain aqueous dispersions of particles. Hereinafter, particles prepared using aqueous solutions of Tween20 and a phospholipid containing 0, 5.2 or 52 mg of albumin are referred to as PNP30, PNP30-Alb-L and PNP30-Alb-H, respectively.

The average particle sizes (cumulant values) of PNP30, PNP30-Alb-L and PNP30-Alb-H were 122 nm, 134 nm and 80 nm, respectively.

The $\lambda_{max}$ of the absorbance of ICG in PNP30 PNP30-Alb-L and PNP30-Alb-H were 784 nm, 790 nm and 797 nm, respectively. It was indicated that the $\lambda_{max}$ was shifted to the long wavelength side by adding albumin, and ICG was adsorbed to albumin.

Subsequently, the numbers of albumin molecules in PNP30-Alb-L and PNP30-Alb-H were evaluated using Micro BCA™ Protein Assay Kit (Thermo Scientific). The results showed that, assuming the number of albumin molecules in PNP30 as 0, PNP30-Alb-L had approximately 200 albumin molecules contained in the surface of each particle, and PNP30-Alb-H had approximately 800 albumin molecules contained in the surface of each particle.

Example 34

Evaluation of Stability of Particles in PBS

Figure 10:
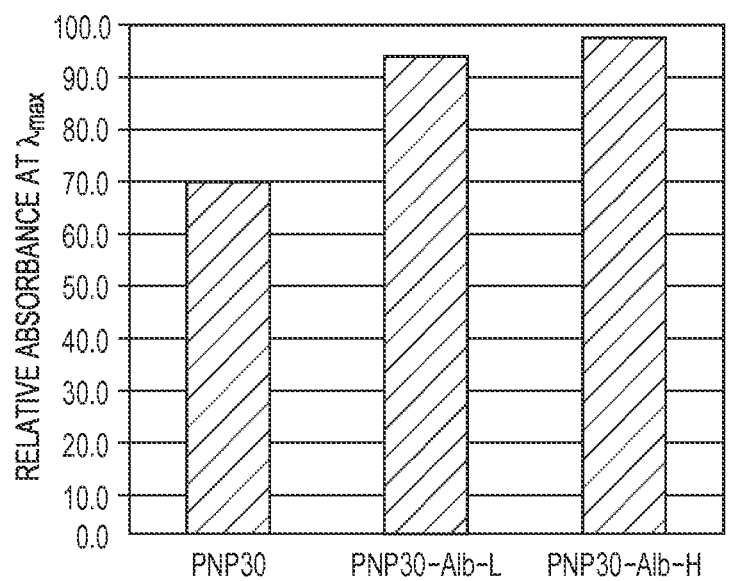
FIG. 10 is a graph illustrating changes with time in the absorbances of PNP30, PNP30-Alb-L and PNP30-Alb-H in PBS at $\lambda_{max}$.

PNP30, PNP30-Alb-L and PNP30-Alb-H were allowed to stand in phosphate-buffered physiological saline (PBS; pH=7.4) at room temperature for one day, and the absorbance at $\lambda_{max}$ of each particle was measured over time to evaluate these particles for properties of ICG leakage and discoloration of in PBS. FIG. 10 illustrates relative absorbances of the particles after one day assuming the absorbance of each particle at $\lambda_{max}$ at zero hour as 100. As shown in FIG. 10, the absorbance of PNP30 was decreased to approximately 70% after one day as compared with the absorbance at zero hour, whereas the absorbances of PNP30-Alb-L and PNP30-Alb-H were maintained above 90%. From the above results, it was demonstrated that PNP30-Alb-L and PNP30-Alb-H stably supported ICG in PBS.

Reference Example [A-1]

11 mg of ICG (Pharmaceutical and Medical Device Regulatory Science of Japan) was dissolved in 4 mL of methanol. 34.7 mg of nicotinamide, which is 20 times (mole ratio) the amount of the ICG, was dissolved in the 4 mL of methanol. These methanol solutions were mixed and stirred for 15 minutes to distill off methanol with an evaporator. 4 mL of chloroform was added to the residue, and the mixture was stirred. Furthermore, ultrasonic irradiation was performed with an ultrasonic dispersion apparatus for 30 seconds. Filtration was performed using a filter having a pore size of 0.45 μm to collect the dissolved component. Hereinafter, the collected sample is also referred to as A-1.

Reference Examples [A-2] and [A-3] [Control]

Samples A-2 and A-3 were obtained in the same manner as in Reference Example (A-1), except that benzyl nicotinate and pyridine were used instead of nicotinamide.

Reference Example [A-0]

A control sample A-0 was obtained in the same manner as in Reference Example (A-1), except that nicotinamide was not used.

Reference Example [A-4] [Control]

A control sample A-4 was obtained in the same manner as in Reference Example (A-1), except that tetrabutylammonium iodide used in the NPL 2 was used instead of nicotinamide.

Reference Examples [B-1] and [B-2]

Samples B-1 and B-2 were obtained in the same manner as in Reference Examples (A-1) and (A-2), except that dichloromethane was used instead of chloroform.

Reference Example [B-0] [Control]

A control sample B-0 was obtained in the same manner as in Reference Example (B-1), except that nicotinamide was not used.

Reference Example [B-5] [Control]

A control sample B-5 was obtained in the same manner as in Reference Example (B-0), except that a mixture solution of dichloromethane and methanol (3:1) was used instead of dichloromethane.

Reference Example [B-6] [Control]

A control sample B-6 was obtained in the same manner as in Reference Example (B-0), except that a mixture solution of dichloromethane and methanol (1:1) was used instead of dichloromethane.

Reference Example [B-7] [Control]

A control sample B-7 was obtained in the same manner as in Reference Example (B-0), except that a mixture solution of dichloromethane and methanol (1:3) was used instead of dichloromethane.

Reference Examples [C-1], [C-2] and [C-3]

Samples C-1, C-2 and C-3 were obtained in the same manner as in Reference Example (A-1), except that fursultiamine, prosultiamine or thiamin disulfide, respectively, was used instead of nicotinamide.

(Evaluation of Solubility of Reference Examples)

Figure 11A:
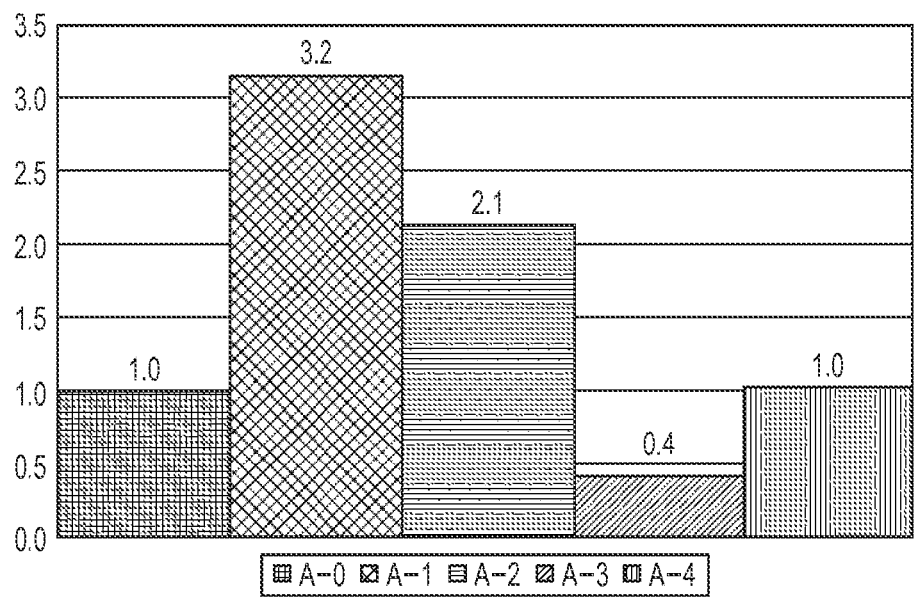
FIGS. 11A and 11B are graphs illustrating results of evaluating the solubility of hydrophilic dyes having a sulfonate group in a hydrophobic solvent.

The samples collected in the above Reference Examples (A-0) to (A-4) were diluted 1.000-fold, and UV-VIS-NIR was measured by a usual method. The absorbances from 550 to 950 nm were accumulated. Comparison with the absorbance of A-0 normalized as 1 is illustrated in FIG. 11A.

Compared with the control sample A-0, which includes a dye and a hydrophobic solvent, the sample A-1 obtained using nicotinamide and the sample A-2 obtained using benzyl nicotinate had very favorable solubility, with the solubility of the sample A-1 being 3.2 times and the solubility of the sample A-2 being 2.1 times that of the solubility of the control sample A-0.

Furthermore, the sample A-1 obtained using nicotinamide and the sample A-2 obtained using benzyl nicotinate had very favorable solubility compared with the sample A-4 obtained using tetrabutyl ammonium salt used in the NPL 2, with the solubility of the sample A-1 being 3.2 times and the solubility of the sample A-2 being 2.1 times that of the solubility of the sample A-4.

The sample A-3 obtained using pyridine did not show efficacy.

Figure 11B:
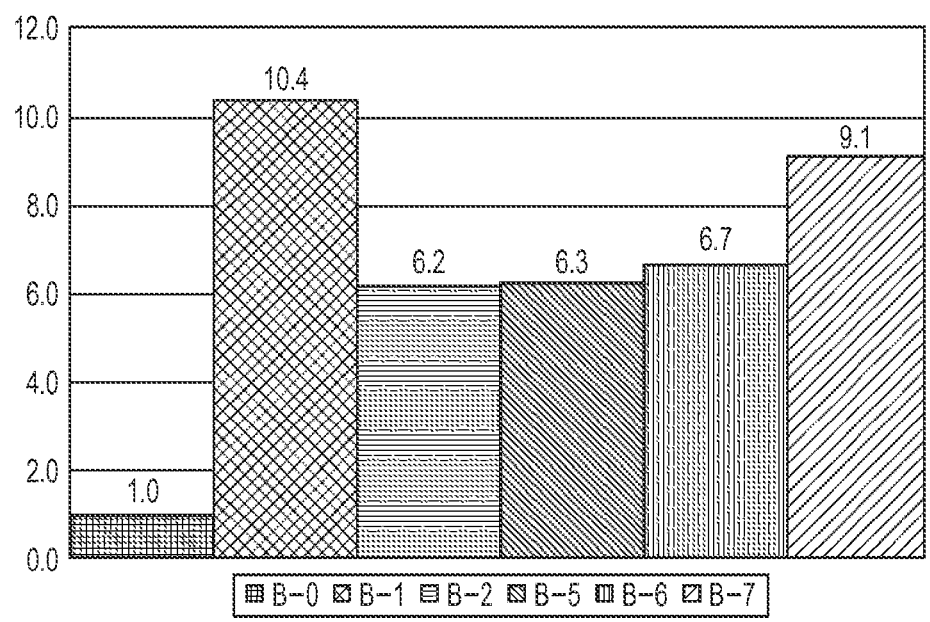

The samples collected in the above Reference Examples (B-0) to (B-7) were diluted 1,000-fold, and UV-VIS-NIR was measured by a usual method. The absorbances from 550 to 950 nm were accumulated. Comparison with the absorbance of B-0 normalized as 1 is illustrated in FIG. 11B.

Compared with the control composition B-0, which includes a dye and a hydrophobic solvent, the sample B-1 obtained using nicotinamide and the sample B-2 obtained using benzyl nicotinate had very favorable solubility, with the solubility of the sample B-1 being 10.4 times and the solubility of the sample B-2 being 6.2 times that of the solubility of the control sample B-0.

Compared with the control composition B-0, the samples B-5, B-6 and B-7 obtained using methanol had very favorable solubility, with 6.3 to 9.1 times the solubility of the control sample B-0 depending on the addition amount of methanol.

The solutions C-1 to C-3, A-0 collected in the above Examples and Comparative Example were diluted 1,000-fold, and UV-VIS-NIR was measured by a usual method. The absorbances from 550 to 950 nm were accumulated and compared with the absorbance of A-0 normalized as 1.

Compared with the control composition A-0, which includes a dye and a hydrophobic solvent, the sample C-1 obtained using fursultiamine, the sample C-2 obtained using prosultiamine and the sample C-3 obtained using thiamin disulfide had very favorable solubility, with the solubility of the sample C-1 being 1.4 times, the solubility of the sample C-2 being 1.6 times and the solubility of the sample C-3 being 1.9 times that of the solubility of the control sample A-0.

Example 35

Synthesis of Polymer Nanoparticle 31

5.5 mg of ICG was dissolved in 1 mL of methanol. As an ICG solubilizer, 58.7 mg of fursultiamine was dissolved in 1 mL of methanol. This fursultiamine-methanol solution was added, the mixture was stirred for 15 minutes, and the solvent was distilled off. 2.0 mL of chloroform was added to the obtained sample, dispersed and dissolved, and then filtered with a having a filter pore size of 0.45 μm. PLGA (40 mg) was added to the sample obtained by filtration and dissolved to prepare a chloroform solution.

180 mg of Tween20 and 22.0 mg of SUNBRIGHT DSPE-020CN were added to 20 mL of ultrapure water as surfactants to prepare a surfactant-dissolved aqueous solution. While this surfactant-dissolved aqueous solution was stirred, the chloroform solution prepared in this Example was added dropwise to prepare a preparatory solution for emulsion.

Using an ultrasonic homogenizer (UD-200; Tomy Seiko Co., Ltd.), ultrasonic irradiation of the preparatory solution for emulsion was performed for one minute and 30 seconds to prepare an emulsion.

To remove chloroform from the emulsion, chloroform was distilled off with an evaporator to prepare a nanoparticle dispersion.

An excess surfactant and the like were removed from the obtained nanoparticle dispersion using a dialysis membrane (fraction molecular weight, 300,000) to obtain a polymer nanoparticle 31. Hereinafter, this polymer nanoparticle is referred to as PNP31.

Example 36

Synthesis of Polymer Nanoparticles 32 and 33

Polymer nanoparticles 32 and 33 were synthesized in the same manner as in Example 35, except that prosultiamine and thiamin disulfide were used instead of fursultiamine. Hereinafter, these polymer nanoparticles are referred to as PNP32 and PNP33.

The polymer nanoparticles 31, 32 and 33 were evaluated for photoacoustic signal characteristics at a wavelength of 790 nm. Table 7 shows the absorption maximum wavelength, the particle sizes, the molar absorbance coefficient per particle, and the photoacoustic signal intensity per particle of the polymer nanoparticles 31, 32 and 33. The molar absorbance coefficient per particle and the photoacoustic signal intensity per particle were converted assuming that the particle size is 100 nm, and compared.

TABLE 7

| Polymer nano-particle | Additive | Maximum absorption (nm) | Average particle size (cumulant) (nm) | Molar absorbance coefficient converted assuming particle size of 100 nm ($M^{-1}cm^{-1}$) | PA signal converted assuming particle size of 100 nm ($VJ^{-1}M^{-1}$) |
|---|---|---|---|---|---|
| PNP31 | Fursultiamine | 794 | 151.9 | $7.6 \times 10^8$ | $1.2 \times 10^{10}$ |
| PNP32 | Prosultiamine | 794 | 141.9 | $1.6 \times 10^9$ | $2.6 \times 10^{10}$ |
| PNP33 | Thiamine disulfide | 795 | 126.7 | $1.2 \times 10^9$ | $2.1 \times 10^{10}$ |

Example 37

Synthesis of Polymer Nanoparticle 34

5.5 mg of ICG was dissolved in 1 mL of methanol, then 50.6 mg of prosultiamine was added as an ICG solubilizer, the mixture was stirred for 15 minutes, and then the solvent was distilled off. 3.0 mL of acetone was added to the obtained sample, and the mixture was filtered with a filter having a pore size of 0.45 μm. PLGA (40 mg) was added to the sample (2.0 mL) obtained by filtration to prepare an organic solvent dispersed solution.

Tween20 (50 mg) was added to 10 mL of ultrapure water as a surfactant to prepare a surfactant-dispersed aqueous solution. While this surfactant-dispersed aqueous solution was stirred, the organic solvent dispersion prepared in this Example was added dropwise to prepare a nanoparticle dispersion.

An excess surfactant and the like were removed from the obtained nanoparticle dispersion with a dialysis membrane (fraction molecular weight, 1,000,000) to obtain a polymer nanoparticle 34. Hereinafter, this polymer nanoparticle is referred to as PNP34.

Example 38

Synthesis of Polymer Nanoparticle 35

A polymer nanoparticle 35 was synthesized in the same manner as in Example 37, except that acetonitrile was used instead of acetone. Hereinafter, this polymer nanoparticle is referred to as PNP35.

Example 39

Synthesis of Polymer Nanomicroparticle 36

IR-820 (5.5 mg; Sigma-Aldrich Japan) was dissolved in 1 mL of methanol to prepare an IR-820-methanol solution. DSPC (9 mg) was dissolved in 1 mL of chloroform to prepare a DSPC-chloroform solution. 1 mL of the IR-820-methanol solution and 1 mL of the DSPC-chloroform solution were mixed, the mixture was stirred for five minutes, and then the solvent was distilled off under reduced pressure at 40° C. IR820 and DSPC evaporated to dryness were completely dissolved in 1.6 mL of chloroform to prepare an IR-820 composition containing IR820 and DSPC dissolved in chloroform. PLGA (20 mg) was dissolved in this composition to prepare a PLGA-chloroform solution. Subsequently, the PLGA-chloroform solution was added to an aqueous solution (20 mL) containing Tween20 (60 mg) and N-(Carbonyl-methoxypolyethyleneglycol 2000)-1,2-distearoyl-sn-glycero-3-phosphoethanolamine, sodium salt (7.3 mg; DSPE-020CN; NOF Corporation) which is a polyethylene glycolated phospholipid having a methoxy group at an end, dissolved therein to prepare a mixture solution, and this mixture solution was stirred at room temperature for three minutes. Then, the mixture solution was treated with an ultrasonic homogenizer for 90 seconds to prepare an O/W-type emulsion. Subsequently, pressure of this emulsion was reduced with a rotary evaporator at 40° C. for two hours to distill off chloroform from the emulsion solution. Then, the solution was thoroughly dialyzed against water and filtered with a filter (pore size, 0.2 μm) to obtain an aqueous dispersion of a polymer nanomicroparticle 36 containing IR-820 and DSPC.

The average particle size and the zeta potential of the polymer nanomicroparticle 36 in water were measured with a Zetasizer nano (Malvern Instruments Ltd.). The average particle size of the polymer nanomicroparticle 36 was 94 nm (cumulant). The zeta potential was −24 mV. Furthermore, UV-VIS-NIR was measured by a usual method. The results showed that the polymer nanomicroparticle 36 had maximum absorption at 825 nm, and the molar absorbance coefficient at the maximum absorption was $5.0 \times 10^9$ $M^{-1}cm^{-1}$.

Photoacoustic signal intensity was measured by the above-described photoacoustic measurement method. The photoacoustic signal intensity of the polymer nanomicroparticle 36 was $1.8 \times 10^{11}$ $VJ^{-1}M^{-1}$ at 750 and 820 nm.

Comparative Example 1

The same amount of ICG as the amount of ICG dissolved in acetone in Example 37 was dissolved in 0.67 mL of methanol, and 1.33 mL of acetone and PLGA (40 mg) were added to prepare an organic solvent-dispersed solution. Except these conditions, a control polymer nanoparticle VBC-1 was synthesized in the same manner as in Example 37.

Comparative Example 2

The same amount of ICG as the amount of ICG dissolved in acetonitrile in Example 38 was dissolved in 0.67 mL of methanol and mixed in 1.33 mL of acetonitrile, and PLGA (40 mg) was added to prepare an organic solvent-dispersed solution. Except these conditions, a control polymer nanoparticle VBC-2 was synthesized in the same manner as in Example 38.

Table 8 shows the absorption maximum wavelength, the particle size, the molar absorbance coefficient per particle, and photoacoustic signal intensity per particle of the polymer nanoparticles PNP34 and PNP35 and the control polymer nanoparticles VBC-1 and VBC-2.

The molar absorbance coefficient per particle and the photoacoustic signal intensity per particle were converted assuming that the particle size is 100 nm.

TABLE 8

| Polymer nanoparticle | Polydispersity index | Additive | Maximum absorption (nm) | Average particle size (cumulant) (nm) | Molar absorbance coefficient converted assuming particle size of 100 nm ($M^{-1}cm^{-1}$) |
|---|---|---|---|---|---|
| VBC-1 | Acetone | None MeOH | 793 | 190.9 | $1.9 \times 10^8$ |
| PNP34 | Acetone | Prosultiamine | 795 | 126.9 | $5.0 \times 10^8$ |
| VBC-2 | Acetonitrile | None MeOH | 793 | 212.2 | $3.9 \times 10^8$ |
| PNP35 | Acetonitrile | Prosultiamine | 795 | 82.0 | $5.3 \times 10^8$ |

Table 8 indicates that, although the same amount of ICG was charged, the polymer nanoparticles PNP34 and PNP35 containing prosultiamine shows higher concentrations of ICG contained in the particle than the polymer nanoparticles VBC-1 and VBC-2, which did not contain prosultiamine. Furthermore, in the evaluation of photoacoustic characteristics, the polymer nanoparticle PNP34 containing prosultiamine showed a signal 1.9 times more intense than the signal intensity of the polymer nanoparticle VBC-2 not containing prosultiamine.

REFERENCE EXAMPLES

Reference Examples will be described below.

The reagents used in the following Reference Examples 1 to 5 were indocyanine green (ICG; Pharmaceutical and Medical Device Regulatory Science of Japan), distearoyl phosphatidyl choline (DSPC; NOF Corporation), dioleoyl-phosphatidylethanolamine (DOPE; NOF Corporation), distearoylphosphatidylethanolamine (DSPE; NOF Corporation), and distearoylphosphatidylserine (DSPS; NOF Corporation). Of these, DSPC, DSPS and DSPE are saturated fatty acids, and DOPE is an unsaturated fatty acid.

Reference Example 1

Solubility of ICG in Chloroform when Phospholipid was Added

Figure 12A:
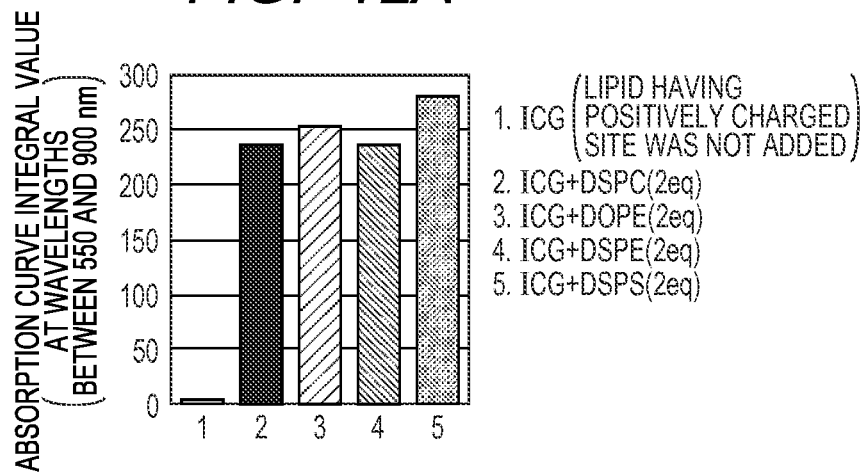
FIGS. 12A and 12B are graphs illustrating results of evaluating the solubility of phospholipid-added ICG in a hydrophobic solvent.

Twice as molar equivalents of a phospholipid was added to 5.5 mg of ICG. As the phospholipid, DSPC, DOPE, DSPE or DSPS was used. These ICG-phospholipid mixtures were dissolved in 3 mL of a methanol-chloroform (1:2) mixture. A control was further prepared by dissolving ICG alone in 3 mL of a methanol-chloroform (1:2) mixture. Subsequently, pressure of these solutions was reduced at 40° C. to distill off the solvent. Each of the ICG-phospholipid mixtures evaporated to dryness were dissolved in 2 mL of chloroform and filtered with a filter having a pore size of 0.2 µm. The filtrates were diluted 100-fold with chloroform. Using a quartz cell having a light path of 1 cm, absorbances were measured wavelengths between 550 and 900 nm in intervals of 1 nm. The sums of absorbances wavelengths between 550 and 900 nm are shown in FIG. 12A as the absorption curve integral values.

Compared with the case where ICG alone was dissolved in chloroform, the solubility of ICG in chloroform was improved approximately 50 times when DSPC, DOPE, DSPE or DSPS was added.

Reference Example 2

Figure 12B:
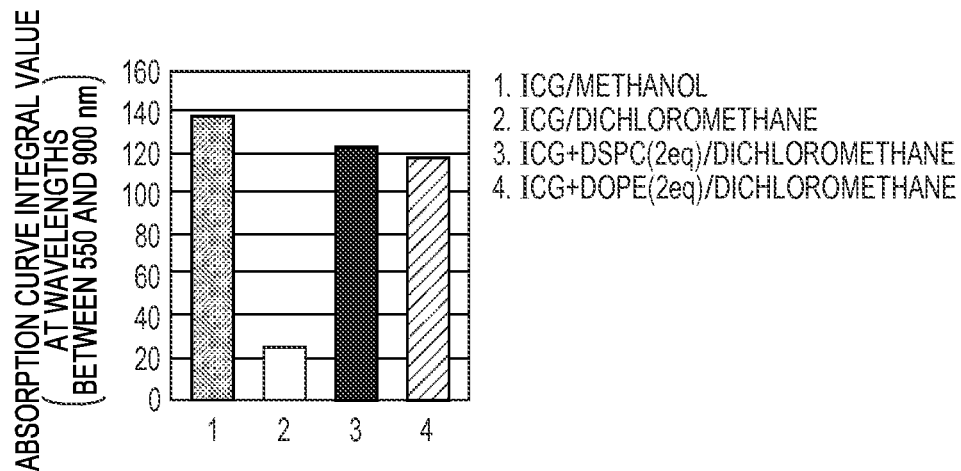

Solubility of ICG in Dichloromethane when Phospholipid was Added 2 molar equivalents of a phospholipid was added to 5.5 mg of ICG. As the phospholipid, DSPC or DOPE was used. Each of these ICG-phospholipid mixtures was dissolved in 2 mL of dichloromethane. Controls were prepared by dissolving in ICG in methanol or dichloromethane. All these ICG solutions were filtered with a filter having a pore size of 0.2 µm and then diluted 500-fold with dichloromethane. The absorption curve integral values obtained in the same manner as in Reference Example 1 are shown in FIG. 12B.

Compared with the cases where ICG alone was dissolved in dichloromethane, the solubility of ICG in dichloromethane was improved approximately six times when DSPC or DOPE was added, and ICG was dissolved to a similar extent as the ICG dissolved methanol. Furthermore, the absorption curve integral values of the ICG-methanol solution (2.75 mg/mL=3.5 mM) and the absorption curve integral values of the ICG-dichloromethane solution were compared. It was inferred that approximately 0.6 mM ICG was dissolved in dichloromethane when a phospholipid is not added.

Reference Example 3

Preparation of ICG-Phospholipid Chloroform Solution

A phospholipid was added to 5.5 mg of ICG in a mole ratio of 1:2. As the phospholipid, DSPC, DSPS, DSPE or DOPE was used. Each of these ICG-phospholipid mixtures was dissolved in 2 mL of chloroform and filtered with a filter having a pore size of 0.45 µm, and then suitably diluted with methanol. The absorption curve integral values at wavelengths between 550 and 950 nm were obtained in the same manner as in Reference Example 1. The absorption curve integral value was converted to a concentration by the following equation 1 to obtain an ICG concentration. In the Equation (1), the multiple correlation coefficient was 0.9999. The results are shown in Table 9.

$$Y = 0.0272X + 1.5834 \quad \text{(Equation 1)}$$

TABLE 9

|  | ICG concentration (mg/ml) |
|---|---|
| ICG + DSPC(2eq) | 1.4 |
| ICG + DSPS(2eq) | 1.1 |
| ICG + DSPE(2eq) | 0.65 |
| ICG + DOPE(2eq) | 1.6 |

Reference Example 4

Preparation of Solution of ICG and Phospholipid in Dichloromethane 2 molar equivalents of a phospholipid was added to 5.5 mg of ICG. As the phospholipid, DSPC, DSPS or DOPE was used. Each of these ICG-phospholipid mixture was dissolved in 2 mL of dichloromethane and filtered with a filter having a pore size of 0.45 µm. The ICG concentration was obtained in the same manner as in Reference Example 3. The results are shown in Table 10.

TABLE 10

|  | ICG concentration (mg/ml) |
|---|---|
| ICG + DSPC(2eq) | 3.1 |
| ICG + DSPS(2eq) | 2.1 |
| ICG + DOPE(2eq) | 2.1 |

Reference Example 5

Composition Ratio of Phospholipid and ICG 0.5, 1 or 2 molar equivalents of DSPC was added to 5.5 mg of ICG.

3 mL of chloroform was added to each of these ICG-DSPC mixtures. The mixtures were heated at 40° C. for two minutes, and ultrasonic irradiation was performed for one minute. However, ICG was not completely dissolved. These suspensions were filtered with a filter having a pore size of 0.45 µm to remove insoluble matters. Each of the filtrates was diluted 3000-fold with methanol. The ICG concentration was obtained in the same manner as in Reference Example 3. The results are shown in Table 11.

TABLE 11

| ICG:DSPC | Addition amount of DSPC mM | Addition amount of ICG mM | Concentration of ICG dissolved (measured value) mM |
|---|---|---|---|
| 1:0.5 | 11.8 | 23.6 | 3.5 |
| 1:1 | 23.6 | 23.6 | 7.4 |
| 1:2 | 47.2 | 23.6 | 15.7 |

As shown in Table 11, it was demonstrated that ICG was dissolved dependently on the DSPC concentration. It was also demonstrated that a composition containing ICG dissolved at a concentration of 15.7 mM could be prepared when 47.2 mM DSPC existed in the ICG chloroform solution.

Reference Example 6

Solubility of IR-820 in Chloroform when DSPC was Added

Twice as molar equivalents of DSPC was added to IR-820 (5.5 mg). 3 mL of methanol-chloroform mixture (methanol:chloroform=1:2) was added to the obtained IR-820-DSPC mixture and dissolved. A control was further prepared by dissolving IR-820 alone in 3 mL of a methanol-chloroform mixture (methanol:chloroform=1:2).

Subsequently, the solvent was distilled off from these prepared solutions under reduced pressure at 40° C. A mixture of IR-820 and DSPC evaporated to dryness was dissolved in 2 mL of chloroform and filtered with a filter having a pore size of 0.2 μm. The filtrates were diluted 100- to 1,000-fold with chloroform. Using a quartz cell having a light path of 1 cm, absorbances at wavelengths between 550 and 900 nm were measured at intervals of 1 nm. The sum of the absorbances at wavelengths between 550 and 900 nm was obtained as absorption curve integral value. Compared with the case where IR-820 alone was dissolved in chloroform, solubility of IR-820 in chloroform was improved approximately 27 times when DSPC was added.

These results indicate that a contrast agent for optical imaging obtained by mixing DSPC, which is a lipid having a positively charged region, IR-820, chloroform, a composition having a polymerizable monomer or a prepolymer and water and polymerizing the polymerizable monomer or the prepolymer contains IR-820 in a large amount. Furthermore, it is considered that since DOPE, DSPE and DSPS are also lipids having a positively charged region, a contrast agent for optical imaging that contains IR-820 in a large amount can be similarly obtained.

Example 40

Synthesis and Evaluation of Characteristics of Polymer Nanoparticles 37 to 44

Polymer nanoparticles 37 to 44 were obtained in the same manner as in Example 11, except that the hydrophobic polymers shown in Table 12 below were used instead of PLGA used in Example 11. These polymer nanoparticles are referred to as PNP37 to PNP44. PNP44 was obtained by adding 10 mg each of poly-L-lactic acid (PLLA) and poly-D-lactic acid (PDLA). All the particles had an average particle size (cumulant) of approximately 100 nm and a molar absorption coefficient between $2 \times 10^9$ and $5 \times 10^9$ $M^{-1}cm^{-1}$.

TABLE 12

| Polymer nanoparticle | Hydrophobic polymer | Average molecular weight | Lactic acid:glycolic acid | Average particle size (nm) | Molar absorption coefficient ($M^{-1}cm^{-1}$) |
|---|---|---|---|---|---|
| PNP37 | PLGA (Durect Corporaiton) | 50,000 | 50:50 | 137.9 | $2.7 \times 10^9$ |
| PNP38 | PLGA (Sigma-Aldrich Japan) | 4,000~15,000 | 75:25 | 111.8 | $2.2 \times 10^9$ |
| PNP39 | PLGA (Sigma-Aldrich Japan) | 66,000~107,000 | 75:25 | 122.5 | $3.3 \times 10^9$ |
| PNP40 | PLA (Wako Pure Chemical Industries, Ltd.) | 20,000 | 100:0 | 122.5 | $1.9 \times 10^9$ |
| PNP41 | PLA (Sigma-Aldrich Japan) | 50,000 | 100:0 | 125.9 | $3.5 \times 10^9$ |
| PNP42 | PLA (Sigma-Aldrich Japan) | 100,000 | 100:0 | 106.3 | $2.1 \times 10^9$ |
| PNP43 | PS (Polyscience Inc.) | 20,000 | N.A. | 126.9 | $4.5 \times 10^9$ |
| PNP44 | PLLA (Sigma-Aldrich Japan) + PDLA (Sigma-Aldrich Japan) | 100,000 | 100:0 | 130.6 | $4.2 \times 10^9$ |

Example 41

Synthesis and Evaluation of Characteristics of Polymer Nanoparticles 45 to 51

Cholesterol in the amounts shown in Table 13 below was added to the ICG chloroform solution prepared in Example 11, and polymer nanoparticles 45 to 51 were prepared in the same manner as in Example 11. These polymer nanoparticles are referred to as PNP45 to PNP51. In preparation of PNP51, cholesterol was precipitated during emulsification, and the particle could not be synthesized.

The average particle size (cumulant) of the particles increased depending on the amount of cholesterol. The molar absorption coefficient increased depending on the average particle size. The maximum molar absorption coefficient was $1.8 \times 10^{10}$ $M^{-1}cm^{-1}$.

TABLE 13

| Polymer nanoparticle | Addition amount of cholesterol (mg) | Average particle size (nm) | Molar absorption coefficient (M$^{-1}$cm$^{-1}$) |
| --- | --- | --- | --- |
| PNP45 | 1.5 | 114.0 | 2.7 × 10$^9$ |
| PNP46 | 3 | 115.7 | 3.4 × 10$^9$ |
| PNP47 | 30 | 113.4 | 1.5 × 10$^9$ |
| PNP48 | 60 | 130.5 | 2.5 × 10$^9$ |
| PNP49 | 90 | 157.8 | 3.2 × 10$^9$ |
| PNP50 | 150 | 285.7 | 1.8 × 10$^{10}$ |
| PNP51 | 300 | — | — |

Example 42

Synthesis and Evaluation of Characteristics of Polymer Nanoparticles 52 to 62

Polymer nanoparticles 52 to 62 were obtained in the same manner as in Example 11, except that PEG phospholipids shown in Table 14 below were used instead of the PEG phospholipid (DSPE-020CN) used in Example 11. These polymer nanoparticles are referred to as PNP52 to PNP62. All the particles had an average particle size (cumulant) of approximately 100 nm and a molar absorption coefficient between 2×10$^9$ and 6×10$^9$ M$^{-1}$ cm$^{-1}$. The PEG phospholipids used in this Example were each manufactured by NOF Corporation.

TABLE 14

| Polymer nano-particle | Phospholipid region of PEG phospholipid | Molecular weight of PEG | Addition of Tween20 (+, added; –, not added) | Average particle size (nm) | Molar absorption coefficient (M$^{-1}$cm$^{-1}$) |
| --- | --- | --- | --- | --- | --- |
| PNP52 | DSPE | 5,000 | + | 105.9 | 2.3 × 10$^9$ |
| PNP53 | DSPE | 10,000 | + | 114.3 | 6.6 × 10$^9$ |
| PNP54 | DSPE | 20,000 | + | 129.3 | 5.9 × 10$^9$ |
| PNP55 | DSPE | 2,000 | – | 100.0 | 3.1 × 10$^9$ |
| PNP56 | DSPE | 5,000 | – | 115.1 | 4.9 × 10$^9$ |
| PNP57 | DSPE | 10,000 | – | 125.2 | 4.7 × 10$^9$ |
| PNP58 | DSPE | 20,000 | – | 152.0 | 6.7 × 10$^9$ |
| PNP59 | DPPE | 2,000 | + | 112.1 | 4.2 × 10$^9$ |
| PNP60 | DPPE | 5,000 | + | 114.7 | 3.9 × 10$^9$ |
| PNP61 | DPPE | 2,000 | – | 97.1 | 2.3 × 10$^9$ |
| PNP62 | DPPE | 5,000 | – | 109.9 | 3.2 × 10$^9$ |

The DPPE(SUNBRIGHT PP-020CN, SUNBRIGHT) is represented by the following chemical formula 13.

In the formula below, $R_1$ and $R_2$ is an alkyl group having 16 carbon atoms.

Formula 13

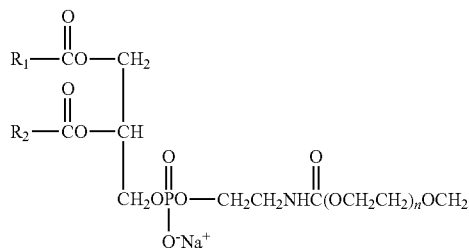

Example 43

Synthesis and Evaluation of Characteristics of Polymer Nanoparticle 63

A polymer nanoparticle 63 was obtained in the same manner as in Example 11, except that the PEG phospholipid (DSPE-020CN) used in Example 11 was used in an addition amount 20 times the addition amount in Example 11, and that an aqueous solution not containing Tween20 was used. This polymer nanoparticle is referred to as PNP63. The average particle size (cumulant) of PNP63 was 99 nm, and the molar absorption coefficient was 9.1×10$^8$ M$^{-1}$cm$^{-1}$.

Example 44

Synthesis and Evaluation of Characteristics of Polymer Nanoparticles 64 to 66

The hydrophobic polymers (20 mg) shown in Table 15 below were dissolved in the ICG composition 2 (1.6 mL) described in Example 2 to prepare chloroform solutions. When the hydrophobic polymers were dissolved, ultrasonic irradiation was performed for five minutes. Polymer nanoparticles 64 to 66 were further obtained in the same manner as in Example 11, except that the ultrasonic irradiation time during the subsequent preparation of O/W-type emulsions was five minutes. These polymer nanoparticles are referred to as PNP64 to PNP66. The average particle sizes (cumulants) and the molar absorption coefficients of these particles are shown in Table 15. When the absorption spectra of these particles were measured, a new sharp absorption peak around 895 nm was observed in addition to the peak around 790 nm, which was attributable to absorption of the ICG monomer. This absorption seems to be attributable to the J-aggregates of ICG.

TABLE 15

| Polymer nano-particle | Hydrophobic polymer | Average molecular weight | Lactic acid:glycolic acid | Average particle size (nm) | Molar absorption coefficient (M$^{-1}$cm$^{-1}$) |
| --- | --- | --- | --- | --- | --- |
| PNP64 | PLGA | 20,000 | 50:50 | 122.9 | 2.1 × 10$^9$ |
| PNP65 | PLGA | 50,000 | 50:50 | 137.9 | 2.7 × 10$^9$ |
| PNP66 | PLA | 20,000 | 100:0 | 111.8 | 2.2 × 10$^9$ |

Example 45

Synthesis and Evaluation of Characteristics of Polymer Nanoparticle 67

PLGA (20 mg) was dissolved in 1.6 mL of a solution of ICG composition 2 in chloroform described in Example 2 to prepare a chloroform solution 45. Subsequently, the chloroform solution 45 was added to an aqueous solution (20 mL) containing Tween60 (25.5 mg; Tokyo Kasei Kogyo) and a phospholipid (7.3 mg; DSPE-020CN; NOF Corporation) dissolved therein to prepare a mixture solution, and the mixture solution was stirred. Then, the same procedure as in Example 13 was performed to obtain a polymer nanoparticle 67. This polymer nanoparticle is referred to as PNP67. The average particle size (cumulant) of PNP67 was 109 nm. The molar absorption coefficient was 4.7×10$^9$ M$^{-1}$cm$^{-1}$.

Example 46

Synthesis and Evaluation of Characteristics of Polymer Nanoparticles 68 to 72

Polymer nanoparticles were prepared by using an aqueous solution of sodium dodecyl sulfate (hereinafter referred to as SDS) instead of the aqueous solution of Tween20 and a phospholipid used in Example 13.

Aqueous solutions (20 mL) containing 0.2, 104, 2,080, 2,080, and 104 mg of SDS (Kishida Chemical Co., Ltd.) dissolved therein were used to prepare polymer nanoparticles 68 to 72, respectively. The chloroform solution 45 described in Example 45 was added to each of these aqueous solutions, and the same procedure as in Example 13 was performed to obtain polymer nanoparticles 68 to 70.

A polymer nanoparticle 71 was prepared in the same manner as in Example 13, except that chloroform was evaporated by stirring the solution in the water bath at 40° C. for two hours instead of using a rotary evaporator.

A polymer nanoparticle 72 was prepared in the same manner as in Example 13, except that chloroform was evaporated by stirring the solution in the water bath at 40° C. for two hours, and that the dialysis procedure was changed to the ultrafiltration procedure. The ultrafiltration procedure was performed under the following conditions. After chloroform was evaporated, 9 mL of the particle dispersion was placed in Amicon Ultra-15 (Nihon Millipore K.K.) and centrifuged at 5,000 g for 15 minutes to concentrate the dispersion to approximately 0.9 mL. This concentrated solution was diluted with 8.1 mL of water, and the same procedure consisting of centrifugation and dilution with water was repeated four times. In the dilution with water in the last procedure, water was added so as to obtain 4.5 mL of the particle dispersion.

As a result of the above preparation, aqueous dispersions of polymer nanoparticles 68 to 72 having the particle surface protected with SDS and having ICG and DSPC contained in PLGA were obtained. Hereinafter, these polymer nanoparticles are referred to as PNP68 to PNP72. The average particle sizes (cumulants) and the molar absorption coefficients of PNP68 to PNP72 are shown in Table 16.

TABLE 16

| | Unit | Example 46 | | | | |
|---|---|---|---|---|---|---|
| | | PNP68 | PNP69 | PNP70 | PNP71 | PNP72 |
| Average particle size | nm | 105 | 76 | 133 | 110 | 69 |
| Molar absorption coefficient | $\times 10^9$ $M^{-1}cm^{-1}$ | 4.7 | 3.1 | 12 | 3.4 | 0.9 |

Example 47

Synthesis and Evaluation of Characteristics of Polymer Nanoparticles 73 and 74

Polymer nanoparticles were prepared using aqueous solution of polyvinyl alcohol (hereinafter referred to as PVA) instead of the aqueous solution of Tween20 and a phospholipid used in Example 13. Polymer nanoparticles 73 and 74 were prepared by using aqueous solutions (20 mL) containing 800 and 200 mg, respectively, of PVA (average molecular weight, 31,000; saponification rate, 86.7% to 88.7%; Sigma-Aldrich Japan) dissolved therein. The chloroform solution 45 described in Example 45 was added to each of these aqueous solutions.

Particles were prepared by the same preparation method as described in Example 13, except that the dialysis procedure was changed to the ultrafiltration procedure described in Example 46.

As a result, aqueous dispersions of polymer nanoparticles 73 and 74 having the particle surface protected with PVA and having ICG and DSPC contained in PLGA were obtained. Hereinafter, these polymer nanoparticles are referred to as PNP73 and PNP74.

The average particle sizes (cumulants) of PNP73 and PNP74 were 120 and 129 nm, respectively. The molar absorption coefficients of PNP73 and PNP74 were $7.5 \times 10^8$ and $7.0 \times 10^9$ $M^{-1}cm^{-1}$, respectively.

Example 48

Synthesis and Evaluation of Characteristics of Polymer Nanoparticles 75 to 77

Polymer nanoparticles were prepared using an aqueous solution of Tween20 and dextran instead of the aqueous solution of Tween20 and a phospholipid in Example 13. Polymer nanoparticles 75 to 77 were prepared using an aqueous solution (20 mL) containing 60 mg of Tween20 and 40 mg of dextran 40 (average molecular weight, 40,000; Tokyo Kasei Kogyo) dissolved therein. 0.45 mg of iron(III) chloride hexahydrate (Wako Pure Chemical Industries, Ltd.) was further added to the aqueous solution for preparing polymer nanoparticle 76.

Polymer nanoparticles were prepared in the same manner as in Example 13, except the above changes and that the dialysis procedure was changed to the ultrafiltration procedure. The ultrafiltration procedure was performed in the same manner as in Example 46.

0.45 mg of iron(III) chloride hexahydrate was added before the ultrafiltration procedure to prepare polymer nanoparticle 77.

As a result, aqueous dispersions of polymer nanoparticles 75 to 77 having the particle surface protected with Tween20 and dextran and having ICG and DSPC contained in PLGA were obtained. Hereinafter, these polymer nanoparticles are referred to as PNP75 to PNP77.

The average particle sizes (cumulants) of PNP75, PNP76 and PNP77 were 127, 107 and 132 nm, respectively. The molar absorption coefficients of PNP75, PNP76 and PNP77 were $6.5 \times 10^9$, $2.6 \times 10^9$, and $6.5 \times 10^9$ $M^{-1}cm^{-1}$, respectively.

Example 49

Synthesis and Evaluation of Characteristics of Polymer Nanoparticle 78 to 80

Polymer nanoparticles were prepared using an aqueous solution of heparin sodium instead of dextran in Example 48. Polymer nanoparticles 78 to 80 were prepared using an aqueous solution (20 mL) containing 60 mg of Tween20 and 40 mg of a heparin sodium salt (Tokyo Kasei Kogyo) dissolved therein. 0.45 mg of iron(III) chloride hexahydrate (Wako Pure Chemical Industries, Ltd.) was further added to the aqueous solution for preparing polymer nanoparticle 79. Particles were each prepared in the same manner as in Example 48 except the above changes.

0.45 mg of iron(III) chloride hexahydrate was added before the ultrafiltration procedure to prepare polymer nanoparticle 80.

As a result, aqueous dispersions of polymer nanoparticles 78 to 80 having the particle surface protected with Tween20 and heparin and having ICG and DSPC contained in PLGA were obtained. Hereinafter, these polymer nanoparticles are referred to as PNP78 to PNP80.

The average particle sizes (cumulants) of PNP78, PNP79 and PNP80 were 97, 105, and 98 nm, respectively. The molar absorption coefficients of PNP78, PNP79 and PNP80 were $1.6 \times 10^9$, $2.2 \times 10^9$ and $1.5 \times 10^9$ $M^{-1}cm^{-1}$, respectively.

Example 50

Synthesis and Evaluation of Characteristics of Polymer Nanoparticles 81 to 83

An ICG composition was prepared using 4.4 mg of ICG and 90 mg of DSPC described in Example 2, and PLGA (20 mg) was dissolved to prepare a chloroform solution. Subsequently, the chloroform solution was added to an aqueous solution (20 mL) containing a phospholipid (DSPE-020CN; NOF Corporation) to obtain a mixture solution. Then, an O/W-type emulsion was prepared by treating the mixture solution with an ultrasonic homogenizer with ice cooling for 90 seconds. Subsequently, the pressure of the emulsion was reduced with a rotary evaporator (40° C., two hours) to evaporate chloroform from the emulsion, and the solution was filtered with a filter having a pore size of 0.2 μm to obtain aqueous dispersions of polymer nanoparticles 81 to 83 having the particle surface protected with a phospholipid and having ICG and DSPC contained in PLGA. Here, polymer nanoparticles 81 to 83 are particles prepared using aqueous solutions (20 mL) containing 7.3, 0.73 and 0.365 mg, respectively, of a phospholipid. Hereinafter, these polymer nanoparticles are referred to as PNP81 to PNP83. The average particle sizes (cumulants) and the molar absorption coefficients of PNP81 to PNP83 are shown in Table 17.

Example 51

Synthesis and Evaluation of Characteristics of Polymer Nanoparticles 84 to 86

Polymer nanoparticles were prepared in the same manner as in Example 50, except that an aqueous solution containing another phospholipid (DSPE-020PA; NOF Corporation) was used instead of the aqueous solution containing a phospholipid in Example 50. As a result, aqueous dispersions of polymer nanoparticles 84 to 86 having the particle surface protected with a phospholipid and having ICG and DSPC contained in PLGA were obtained. Here, the polymer nanoparticles 84 to 86 were particles prepared using aqueous solutions (20 mL) containing 7.3, 0.73 and 0.365 mg, respectively, of a phospholipid. Hereinafter, these polymer nanoparticles are referred to as PNP84 to PNP86. The average particle sizes (cumulants) and the molar absorption coefficients of PNP84 to PNP86 are shown in Table 17.

Example 52

Synthesis and Evaluation of Characteristics of Polymer Nanoparticles 87 and 88

Polymer nanoparticles were prepared in the same manner as in Example 50, except that an aqueous solution containing Tween20 was used instead of the aqueous solution containing a phospholipid in Example 50. As a result, aqueous dispersions of polymer nanoparticles 87 and 88 having the particle surface protected with Tween20 and having ICG and DSPC contained in PLGA were obtained. Here, polymer nanoparticles 87 and 88 were particles prepared using an aqueous solution (20 mL) containing 6 and 0.6 mg, respectively, of Tween20. Hereinafter, these polymer nanoparticles are referred to as PNP87 and PNP88. The average particle sizes (cumulants) and the molar absorption coefficients of PNP87 and PNP88 are shown in Table 17.

TABLE 17

|  | Unit | Example 50 | | | Example 51 | | | Example 52 | |
| --- | --- | --- | --- | --- | --- | --- | --- | --- | --- |
|  |  | PNP81 | PNP82 | PNP83 | PNP84 | PNP85 | PNP86 | PNP87 | PNP88 |
| Average particle size | nm | 118 | 145 | 141 | 161 | 142 | 143 | 143 | 193 |
| Molar absorption coefficient | $\times 10^9$ $M^{-1}cm^{-1}$ | 2.5 | 5.4 | 5.2 | 8.6 | 5.5 | 5.5 | 5.1 | 13 |

Example 53

Synthesis and Evaluation of Characteristics of Polymer Nanoparticle 89

A polymer nanoparticle was prepared in the same manner as in Example 50, except that an aqueous solution (4.8 mL) containing 0.9 mg of a phospholipid (DSPE-020CN) and 7.2 mg of Tween20 was used instead of the aqueous solution containing only a phospholipid in Example 50. As a result, an aqueous dispersion of polymer nanoparticle 89 having the particle surface protected with a phospholipid and Tween20 and having ICG and DSPC contained in PLGA was obtained. Hereinafter, this polymer nanoparticle is referred to as PNP89. The average particle size (cumulant) of PNP89 was 203 nm. The molar absorption coefficient was $1.4 \times 10^{10}$ $M^{-1}cm^{-1}$.

Example 54

Measurement of the Photoacoustic Signal Intensity of the Polymer Nanoparticles 64 to 66

TABLE 18

| Polymer nanoparticle | PA signal Intensity at 780 nm $(VJ^{-1}M^{-1})$ | PA signal Intensity at 895 nm $(VJ^{-1}M^{-1})$ |
| --- | --- | --- |
| PNP64 | $8.3 \times 10^{10}$ | $2.4 \times 10^{11}$ |
| PNP65 | $1.1 \times 10^{11}$ | $2.6 \times 10^{11}$ |
| PNP66 | $6.5 \times 10^{10}$ | $1.7 \times 10^{11}$ |

The polymer nanoparticles 64 to 66 were evaluated for photoacoustic (PA) signal characteristics at wavelength of 780 nm and 895 nm, respectively. Table 18 shows the photoacoustic signal intensity per a particle ($VJ^{-1}M^{-1}$) of the polymer nanoparticles 64 to 66. The result demonstrated that these nanoparticles enable the generation of the photoacoustic signal at both 790 nm (ICG monomer absorption) and 895 nm (the J-aggregates absorption). The photoacoustic imaging at multiple optical wavelengths can produce quantitative optical absorption reconstructions, which is effective in the improvement of accuracy of the nanoparticle detection in vivo.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-187667, filed Aug. 24, 2010 and Japanese Patent Application No. 2011-086280, filed Apr. 8, 2011 which are hereby incorporated by reference herein in their entirety.

The invention claimed is:

1. A particle comprising a hydrophilic dye having a sulfonate group and a hydrophobic polymer, wherein the particle further comprises a thiamine derivative.

2. The particle according to claim 1, wherein the hydrophilic dye having a sulfonate group is indocyanine green.

3. The particle according to claim 1, wherein the thiamine derivative is represented by formula (II):

X-B—Y     (II), where, in the formula (II), B represents formula (b):

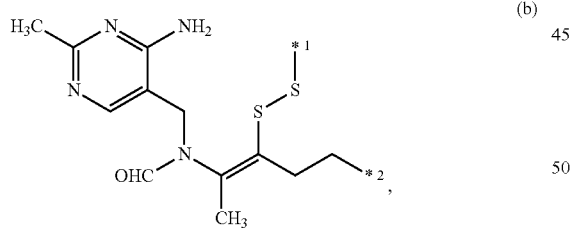

(b)

where, in the formula (b), *1 represents a bonding site bound to X of the formula (II), and *2 represents a bonding site bound to Y of the formula (II);
where, in the formula (II), X represents one of formulae (x1), (x2), (x3) and (x4):

*—(CH₂)ₙ     (x1)

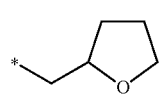

(x2)

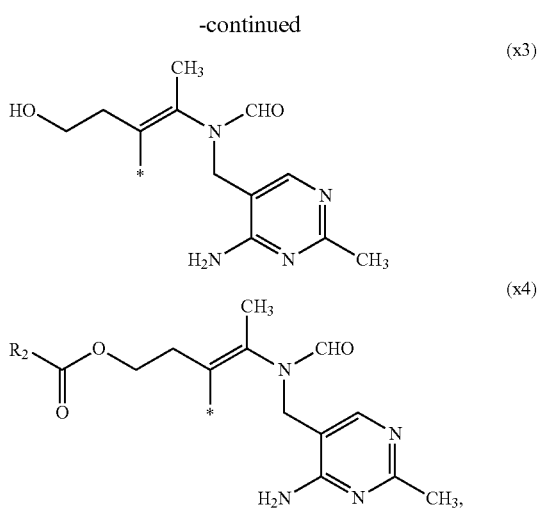

where, in the formulae (x1), (x2), (x3) and (x4), * represents a bonding site bound to B of the formula (II),
where, in the formula (x1), n is an integer selected from 1 to 10,
where the formula (x1) may be substituted by a halogen atom, an alkyl group having 1 to 5 carbon atoms, a hydroxyl group and an amino acid, and
where, in the formula (x4), R₂ is one of a substituted or unsubstituted alkyl group having 1 to 10 carbon atoms and a substituted or unsubstituted benzene; and
where, in the formula (II), Y represents one of formulae (y1) and (y2):

(y1)

-continued

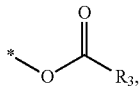
(y2)

where, in the formulae (y1) and (y2), * represents a bonding site bound to B of the formula (II), and where, in the formula (y2), $R_3$ is one of a substituted or unsubstituted alkyl group having 1 to 10 carbon atoms and a substituted or unsubstituted benzene.

4. The particle according to claim 1, wherein the thiamine derivative is at least one of fursultiamine, prosultiamine and thiamin disulfide.

5. The particle according to claim 1, wherein the particle has a surfactant on a surface of the particle.

6. The particle according to claim 5, wherein the surfactant is a surfactant selected from at least one of a polyoxyethylene sorbitan fatty acid ester and a phospholipid.

7. The particle according to claim 1, wherein the particle further has a capture molecule that binds specifically to a target site.

8. The particle according to claim 1, wherein an average particle diameter of the particle is from 10 nm to 1,000 nm.

9. The particle according to claim 1, wherein albumin is noncovalently bonded to a surface thereof.

10. A contrast agent for optical imaging having the particle according to claim 1 and a dispersion medium containing the particle dispersed therein.

11. The particle according to claim 7, wherein the capture molecule comprises an amino acid sequence represented by SEQ ID NO: 2.

12. A particle comprising a hydrophilic dye having a sulfonate group and a hydrophobic polymer,
wherein the particle further comprises a nicotinic acid derivative,
wherein the particle further has a capture molecule that binds specifically to a target site, and
wherein the capture molecule comprises an amino acid sequence represented by SEQ ID NO: 2.

13. The particle according to claim 12, wherein the hydrophilic dye having a sulfonate group is indocyanine green.

14. The particle according to claim 12, wherein the particle has a surfactant on a surface of the particle.

15. The particle according to claim 14, wherein the surfactant is a surfactant selected from at least one of a polyoxyethylene sorbitan fatty acid ester and a phospholipid.

16. The particle according to claim 12, wherein an average particle diameter of the particle is from 10 nm to 1,000 nm.

17. The particle according to claim 12, wherein albumin is noncovalently bonded to a surface thereof.

18. A contrast agent for optical imaging having the particle according to claim 12 and a dispersion medium containing the particle dispersed therein.

19. The particle according to claim 12, wherein the nicotinic acid derivative is represented by formula (I):

$$A\text{-}Z \quad (I),$$

where, in the formula (I), A represents one of formulae (a1), (a2) and (a3):

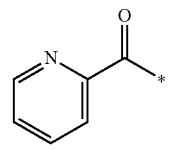
(a1)

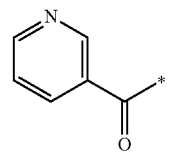
(a2)

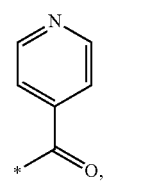
(a3)

where, in the formulae (a1), (a2) and (a3), * represents a bonding site bound to Z of the formula (I); and where, in the formula (I), Z represents one of formulae (z1), (z2) and (z3):

*—NH₂      (z1)

*—OR₁      (z2)

(z3)

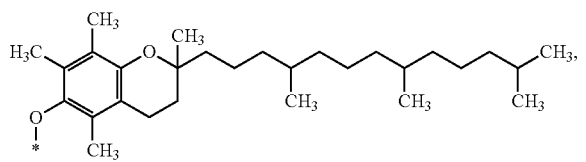

where, in the formulae (z1), (z2) and (z3), * represents a bonding site bound to A of the formula (I), and where, in the formula (z2), $R_1$ is one of a hydrogen atom, a substituted or unsubstituted alkyl group having 1 to 10 carbon atoms and a benzyl group, and the substituent is one of a halogen atom, an alkyl group having 1 to 5 carbon atoms, a hydroxyl group and an amino acid.

20. The particle according to claim 12, wherein the nicotinic acid derivative is nicotinamide.

* * * * *